(12) United States Patent
Braunersreuther et al.

(10) Patent No.: US 11,697,079 B2
(45) Date of Patent: *Jul. 11, 2023

(54) SEPARATION APPARATUS AND USE THEREOF

(71) Applicant: Hoffmann-La Roche Inc., Little Falls, NJ (US)

(72) Inventors: Oskar Braunersreuther, Penzberg (DE); Alexander Jockwer, Eurasburg (DE); Torsten Klabuhn, Bad Heilbrunn (DE); Michael Pohlscheidt, Carlsbad, CA (US); Joerg Thiele, Sindelsdorf (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 207 days.

This patent is subject to a terminal disclaimer.

(21) Appl. No.: 16/899,453

(22) Filed: Jun. 11, 2020

(65) Prior Publication Data

US 2020/0406168 A1 Dec. 31, 2020

Related U.S. Application Data

(63) Continuation of application No. 15/440,350, filed on Feb. 23, 2017, now Pat. No. 10,702,800, which is a
(Continued)

(30) Foreign Application Priority Data

Jan. 17, 2011 (EP) ........................................ 1151110

(51) Int. Cl.
*B01D 21/00* (2006.01)
*C12M 1/26* (2006.01)
(Continued)

(52) U.S. Cl.
CPC ..... *B01D 21/0042* (2013.01); *B01D 21/0045* (2013.01); *B01D 21/0057* (2013.01);
(Continued)

(58) Field of Classification Search
CPC ............ B01D 21/0042; B01D 21/0045; B01D 21/0057; B01D 2221/06; B01D 21/0024;
(Continued)

(56) References Cited

U.S. PATENT DOCUMENTS 2,967,107 A 1/1961 Geiger et al.
3,385,439 A * 5/1968 Bach .................... B01D 21/283
210/522
(Continued)

FOREIGN PATENT DOCUMENTS

DE 3619926 A1 1/1987
EP 0003146 A2 7/1979
(Continued)

OTHER PUBLICATIONS

Derwent Abstract of FR 2878912 (Jun. 2006).
(Continued)

*Primary Examiner* — Joseph W Drodge
(74) *Attorney, Agent, or Firm* — Morrison & Foerster LLP

(57) ABSTRACT

Separating apparatus, comprising a sedimentation settler and a collection vessel disposed underneath and being in fluid communication with the sedimentation settler, the collection vessel forming a receiving chamber having an outlet at or adjacent to the chamber bottom and having an inlet opening, wherein the collection vessel is arranged such the flow direction of the fluid in the area underneath the sedimentation settler is substantially in line with the direction of the channels of the sedimentation settler.

19 Claims, 30 Drawing Sheets

Related U.S. Application Data continuation of application No. 13/942,661, filed on Jul. 15, 2013, now abandoned, which is a continuation of application No. PCT/EP2012/050508, filed on Jan. 13, 2012.

(51) Int. Cl.
*C12M 1/00* (2006.01)
*C12M 1/06* (2006.01)

(52) U.S. Cl.
CPC ............ *C12M 27/02* (2013.01); *C12M 27/20* (2013.01); *C12M 33/22* (2013.01); *C12M 47/02* (2013.01); *B01D 2221/06* (2013.01)

(58) Field of Classification Search
CPC ............ B01D 21/0039; B01D 21/0048; B01D 21/0087; B01D 21/009; B01D 21/24; B01D 21/2444; B01D 21/245; B01D 21/2483; B01D 21/28; B01D 21/283; B01D 2221/10; C12M 27/02; C12M 27/20; C12M 33/22; C12M 47/02; C12M 27/16; C12M 43/00; C12M 47/10; C12M 47/12; C12M 47/20
USPC ......................................... 210/522, 802, 803
See application file for complete search history.

(56) References Cited

U.S. PATENT DOCUMENTS

| | | | | |
|---|---|---|---|---|
| 3,552,554 | A * | 1/1971 | Olgard | ............... B01D 21/0051 210/519 |
| 3,768,648 | A | 10/1973 | Anderson et al. | |
| 3,897,676 | A | 8/1975 | Membrino | |
| 3,898,162 | A | 8/1975 | Carlson et al. | |
| 4,123,365 | A | 10/1978 | Middelbeek | |
| 4,184,954 | A | 1/1980 | Peterson | |
| 4,814,278 | A * | 3/1989 | Hamamoto | ............ C12M 29/10 435/295.1 |
| 5,320,963 | A * | 6/1994 | Knaack | ............ B01D 21/0039 210/615 |
| 5,654,197 | A * | 8/1997 | Jem | ........................ C12M 27/02 435/308.1 |
| 5,817,505 | A * | 10/1998 | Thompson | ............. C12M 33/22 435/813 |
| 5,874,003 | A | 2/1999 | Rose | |
| 9,809,792 | B2 * | 11/2017 | Kauling | ................. C12M 27/16 |
| 10,702,800 | B2 | 7/2020 | Braunersreuther et al. | |
| 2010/0167910 | A1 | 7/2010 | Odueyungbo | |
| 2011/0003331 | A1 * | 1/2011 | Pavia | ..................... C12M 35/04 435/41 |
| 2011/0097800 | A1 * | 4/2011 | Kauling | ................. C12M 33/22 435/293.1 |
| 2017/0157539 | A1 | 6/2017 | Braunersreuther et al. | |

FOREIGN PATENT DOCUMENTS

| | | |
|---|---|---|
| EP | 0003146 A3 | 7/1979 |
| EP | 0061228 A2 | 9/1982 |
| EP | 0259928 A1 | 3/1988 |
| FR | 2878912 A1 | 6/2006 |
| FR | 2880548 A1 | 7/2006 |
| FR | 2880548 B1 | 8/2007 |
| FR | 2878912 B1 | 8/2008 |
| JP | 2005501553 A | 1/2005 |
| WO | 2003020919 A2 | 3/2003 |
| WO | 2003020919 A3 | 10/2003 |
| WO | 2012098055 A1 | 7/2012 |

OTHER PUBLICATIONS

English Abstract of DE3619926, pp. 1-3 (Jan. 2007).
International Preliminary Report On Patentability, dated Jul. 17, 2013, for PCT Application No. PCT/EP2012/050508, filed Jan. 13, 2012, 7 pages.
International Search Report, dated Apr. 10, 2012, for PCT Application No. PCT/EP2012/050508, filed Jan. 13, 2012, 3 pages.
Voisard et al. (2003). "Potential of Cell Retention Techniques for Large-Scale High-Density Perfusion Culture of Suspended Mammalian Cells," Biotechnol. Bioeng. 82(7):751-765.
Written Opinion of the International Searching Authority, dated Apr. 10, 2012, for PCT Application No. PCT/EP2012/050508, filed Jan. 13, 2012, 6 pages.

* cited by examiner

SEPARATION APPARATUS AND USE THEREOF

CROSS REFERENCE TO RELATED APPLICATIONS

This application is a continuation of U.S. patent application Ser. No. 15/440,350, filed Feb. 23, 2017, which is a continuation of U.S. patent application Ser. No. 13/942,661, filed Jul. 15, 2013, which is a continuation of International Application No. PCT/EP2012/050508 having an international filing date of Jan. 13, 2012, the entire contents of each of which are incorporated herein by reference, and which claims benefit under 35 U.S.C. § 119 to European Patent Application No. 11151110.1 filed Jan. 17, 2011.

FIELD OF THE INVENTION

The invention relates to a separation apparatus and its use, e.g. in processes of continuous separation of suspended cells from a suspension, e.g. in a seed train fermentation. Thus, the invention relates to cultivating suspended cells or cell lines.

BACKGROUND OF THE INVENTION

In the art, sedimentation separators are known in order to achieve high viable cell concentrations in suspensions and to remove sensitive products, like highly glycosylated polypeptides and proteins. In one process, sedimentation settlers are used that are inclined from the vertical and comprise a plurality of long and narrow tubes or channels. Larger cells are removed from the suspension by settling onto the upward-facing surfaces of the settler, where they form thin sediment layers that slide down and are collected at the bottom of a vessel located underneath the sedimentation settler. An example of such sedimentation separator is shown in WO 03/020919.

With such sedimentation separator it is always desired to reduce the retention time of the cells in the separation apparatus in order to minimize the time cells and product is maintained under non-controlled conditions, e.g. outside the well controlled bioreactor in an external loop, thus to minimize cell and product damages to the cells. From this perspective, there is a need to have a collection vessel as small as possible. On the other hand, a high throughput is desired, which can be obtained by increasing the inflow volume or flow-through. This, on the other hand is disadvantageous as it may come along with undesirable turbulences of the flow within the collection vessel and can lead to increased dwell times by negative effects on the sedimentation behavior of the cells also negatively affecting process performances.

The potential of cell retention techniques for large-scale high-density perfusion culture of suspended mammalian cells is reported by Voisard, D., et al. (Biotechnol. Bioeng. 82 (2003) 751-765). Chary, S., reported in 2010 the achieving higher titers and higher run-rates through cell culture perfusion operations in the inoculum train (BioProduction Conference, 2010, Barcelona, Spain).

DE-A-36 19 926 describes an apparatus for treating a liquid containing a depositing contamination of solid particles, which apparatus includes at least one chamber through which the liquid can flow and which has liquid feed and outlet connections and which apparatus is furnished with guide surfaces to guide the liquid into the separation chamber. FIG. 2 of DE-A-36 19 926 shows a stationary separator being primarily designed to remove solid particles from water and oil. The separator includes a housing which houses a deposition chamber. The contaminated water is passed through the contaminated water supply and comes in a pre-separation chamber. Throughout the deposition, a low flow rate is adjusted so that the separation of the components occurs by the force of gravity. A portion of the oil collects in the pre-separation chamber already above and can be discharged through the oil drain. A portion of the solids sink to the bottom of the pre-separation chamber and comes down into the deposition chamber. The pre-treated water then flows with low flow rate through a package of dividers upwards.

EP-A-0 003 146 discloses a device for separating water and water-insoluble, light substances contained therein, for example, oil. The device comprises a reservoir for receiving a mixture of water and substances and a plurality of sequential, parallel, sloping separation channels arranged in the reservoir and bounded by channel walls, an inlet chamber, a mixture inlet opening out in the inlet chamber and distributing the mixture at right angles to the plane of the drawing, a feeding chamber communicating with the inlet chamber, a substance outlet, a layer-limit sensor, an overflow with an overflow rim, a water outlet communicating with the overflow and a screen separating the overflow from a collecting space for light substances. The assembly of separation channels is arranged between the feeding chamber and an outlet chamber of the reservoir. The mixture flows through a dosing member, in which flocculation promoting chemicals are added to the mixture and through a mixer towards the mixture inlet. The desired flocculation takes place in the feeding chamber.

Thus, in DE-A-36 19 926 and EP-A-0 003 146 the flow direction of the mixture is parallel to the separation plates, from the upper end of the separation plates towards the lower end of the separation plates, before the mixture enters the separation plates.

SUMMARY OF THE INVENTION

It is an object of the invention to provide a sedimentation apparatus having a short retention time of the cells and at the same time without impairing the separation efficiency. This object is achieved with the features of the claims.

According to a first aspect, the invention provides a separating apparatus comprising a sedimentation settler and a collection vessel. The collection vessel is disposed underneath the sedimentation settler and is also in fluid communication with the sedimentation settler. The collection vessel forms a receiving chamber that has an outlet at or adjacent to the chamber bottom and has an inlet opening. In one embodiment the collection vessel has one inlet opening. The collection vessel is arranged such that the flow direction of the fluid in the area underneath the sedimentation settler is substantially in line with the direction of the channels of the sedimentation settler.

The inflow inlet opening is preferably located at the same vertical height level of the separating apparatus as the lower edge of the sedimentation settler or below. In the first embodiment described below, the inflow inlet opening is preferably located at a vertical height level below the lower edge of the sedimentation settler. On the other hand, in the second embodiment described below, the inflow inlet opening is preferably located at the same vertical height level of the separating apparatus as the lower edge of the sedimentation settler. With such arrangements, the inflow into the collection vessel takes place underneath the lower edge of the sedimentation settler, and at most at the same vertical level as the sedimentation settler.

According to a first embodiment of the first aspect, the invention provides a separating apparatus comprising a sedimentation settler and a collection vessel. The collection vessel is disposed underneath the sedimentation settler and is also in fluid communication with the sedimentation settler. The collection vessel forms a receiving chamber that has an outlet at or adjacent to the chamber bottom and has an inlet opening. In one embodiment the collection vessel has one inlet opening. The inlet opening may be located at the upstanding side wall of the collection vessel. Furthermore, the collection vessel comprises an inflow deflection element.

According to one embodiment, the inlet is below the lower edge of the sedimentation settler. The invention also encompasses that the plates of the sedimentation settler do not extend into the collection vessel.

According to a preferred embodiment of the invention, a single inflow deflection element is provided.

The deflection element is adapted such that the retention or dwell time of a particle and/or the hydraulic dwell time, for example of a cell suspension, in the collection vessel is reduced, for example compared to a separating apparatus having a collection vessel without a deflection element. In particular, the size of the collection vessel and the deflection element are adapted to each other such that the retention or dwell time of a fluid in the collection vessel is reduced compared to a separating apparatus having a collection vessel without a deflection element.

According to an embodiment, the inflow deflection element is located at or in proximity to the inlet opening. It is furthermore encompassed that the deflection element is shaped and arranged such that it downwardly deflects the majority of an inflow of liquid or fluid through the inlet opening. In case the inlet opening is located at the upstanding side wall of the collection vessel, an inflow of liquid or fluid into the receiving chamber will generally flow somewhat towards the bottom of the receiving chamber due to gravity. The deflection element according to the invention provides a controlled deflection of the inflow in a direction to the bottom of the collection chamber without negatively affecting the cells, for example by shear force. Thus, the deflection element impedes the liquid flow to flow along its natural path guided by gravity and urges the stream of liquid to change its direction downwardly. Each of these measures provides that the retention or dwell time of a particle and/or the hydraulic dwell time, for example of a cell suspension, in the collection vessel is reduced, as mentioned above.

The wall of the receiving chamber may be curved such that the horizontal cross-sectional area decreases towards the bottom thereof. For example, the receiving chamber has the shape of an inverse cone or truncated cone, or is cup-shaped or bowl-shaped, i.e. having a curved inner wall allowing to optimize the volume.

The arrangement and shape of the deflection element and the curvature of the receiving chamber may be adapted to each other such that the initially downwardly deflected inflow is further guided up towards the sedimentation settler. Thus, the inflow is deflected downwardly adjacent to the inlet opening, is then guided by the curvature or shape of the inner wall of the receiving chamber further downwards but then follows the cone- or cup-like shape of the vessel and is guided upwards and towards the sedimentation settler.

The inflow deflection element is preferably a baffle plate. The baffle plate is arranged inclined relative to a first imaginary vertical plane being perpendicular to a second imaginary vertical plane comprising the inflow direction axis through the inlet opening. According to an embodiment, the baffle plate is inclined such that it intersects said first imaginary vertical plane along a horizontal line. It is furthermore preferred that the inclination of the baffle plate is the same as the inclination of the sedimentation settler. Such an arrangement provides for the retention or dwell time of a particle and/or the hydraulic dwell time in the collection vessel being reduced.

According to a further embodiment, the baffle plate extends in elongation of the lower end of the sedimentation settler at the lower edge of the sedimentation settler closest to the inlet opening. Alternatively, the baffle plate is connected to the inner wall of the collection vessel above the inlet opening. Such arrangements also provide for the retention or dwell time of a particle and/or the hydraulic dwell time in the collection vessel being reduced.

According to a second embodiment of the first aspect, the invention provides a separating apparatus comprising a sedimentation settler and a collection vessel. The collection vessel is disposed underneath the sedimentation settler and is also in fluid communication with the sedimentation settler. The collection vessel forms a receiving chamber that has an outlet at or adjacent to the chamber bottom and has an inlet opening. Furthermore, the inflow inlet opening is arranged such that the direction of fluid inflow through the inlet opening is parallel to the direction of the sedimentation settler. In a more broader sense, the direction of fluid inflow through the inlet opening deviates from the direction of the sedimentation settler by +/−10°, if seen in a imaginary vertical plane comprising the inflow direction axis through the inlet opening. In other words, the inflow channel through the inlet opening is inclined as is the sedimentation settler. Such an arrangement provides for the retention or dwell time of a particle and/or the hydraulic dwell time in the collection vessel being reduced.

The invention also encompasses the combination of the first and second embodiment of the first aspect of the invention.

According to a further embodiment, the separating apparatus comprises a means for controlling the direction and reducing the velocity of the inflow upstream of the inlet opening. In one embodiment the means is a peripheral equipment means. The means can be for example a flow distributer or reducer of flow velocities known to a person skilled in the art.

The sedimentation settler comprises a plurality of plates forming a plurality sedimentation channels in between. Preferably, the plates of the sedimentation settler, or the entire sedimentation settler, do not reach into the collection vessel from above. That is, the separation apparatus is provided in a modular manner, having the collection vessel as one module, and the sedimenatation settler as another, separate and independent module. This allows for an independent exchange of an individual module (having other dimensions, for example) irrespective of and independent from the other module.

According to a second aspect, the invention provides a separating apparatus comprising a sedimentation settler and a collection vessel. The collection vessel is disposed underneath the sedimentation settler and is also in fluid communication with the sedimentation settler. The collection vessel forms a receiving chamber that has an outlet at or adjacent to the chamber bottom and has an inlet opening. The inlet opening is preferably located at the upstanding side wall of the collection vessel. The separating apparatus further comprises a means for controlling the direction and reducing the velocity of the inflow upstream of the inlet opening.

According to the invention, the provision of a means for controlling the direction and reducing the velocity of the inflow upstream of the inlet opening according to the second aspect may be combined with the first and/or second embodiment of the first aspect.

In one embodiment of the before outlined aspects the separations apparatus has separation area to volume ratio of from 50 $m^2/m^3$ to 60 $m^2/m^3$. In another embodiment the volume flow-through is less than 5 per day. In one embodiment the volume flow through the sedimentation apparatus is of from 500 L/day to 3000 L/day.

The volume of the collection vessel may range from 1 to 20 $m^3$.

A third aspect of the invention relates to a system, in particular a seed-train system, comprising a first fermenter, a separating apparatus according to any of the aspects of the invention located downstream of the first fermenter, and at least a second fermenter located downstream of the separating apparatus. In one embodiment the second fermenter is inoculated with an inoculation cell density of from $5*10^5$ cells/ml to $50*10^5$ cells/ml.

A further aspect of the invention relates to the use of the separating apparatus according to the invention in a seed-train system, comprising a first fermenter located upstream of the first fermenter, and at least a second fermenter located downstream of the separating apparatus. In one embodiment the second fermenter is inoculated with an inoculation cell density of from $5*10^5$ cells/ml to $50*10^5$ cells/ml.

With the invention it is possible to provide a separation apparatus having a collection vessel of comparably small volume in terms of ensuring a minimized residence time but at the same time having a sufficiently high volume flow and separation efficiency. The deflection element provides a controlled flow of the suspension towards the sedimentation settler which is not detrimental to the retention time in the apparatus. The cell suspension flow is deflected by the deflection element such that the flow direction of the suspension after entry into the collection vessel in the area underneath the sedimentation settler is substantially in line with the direction of the channels of the sedimentation settler.

Other aspects, features, and advantages will be apparent from the summary above, as well as from the description that follows, including the figures and the claims.

10,000 L process (black dashed line; inoculation cell density of 100%); 2 L fermentations (♦/ICD 100%); 2 L and 400 L fermentations (○/●/ICD 333%) and 2 L fermentation (■/ICD 666%).

Figure 27:
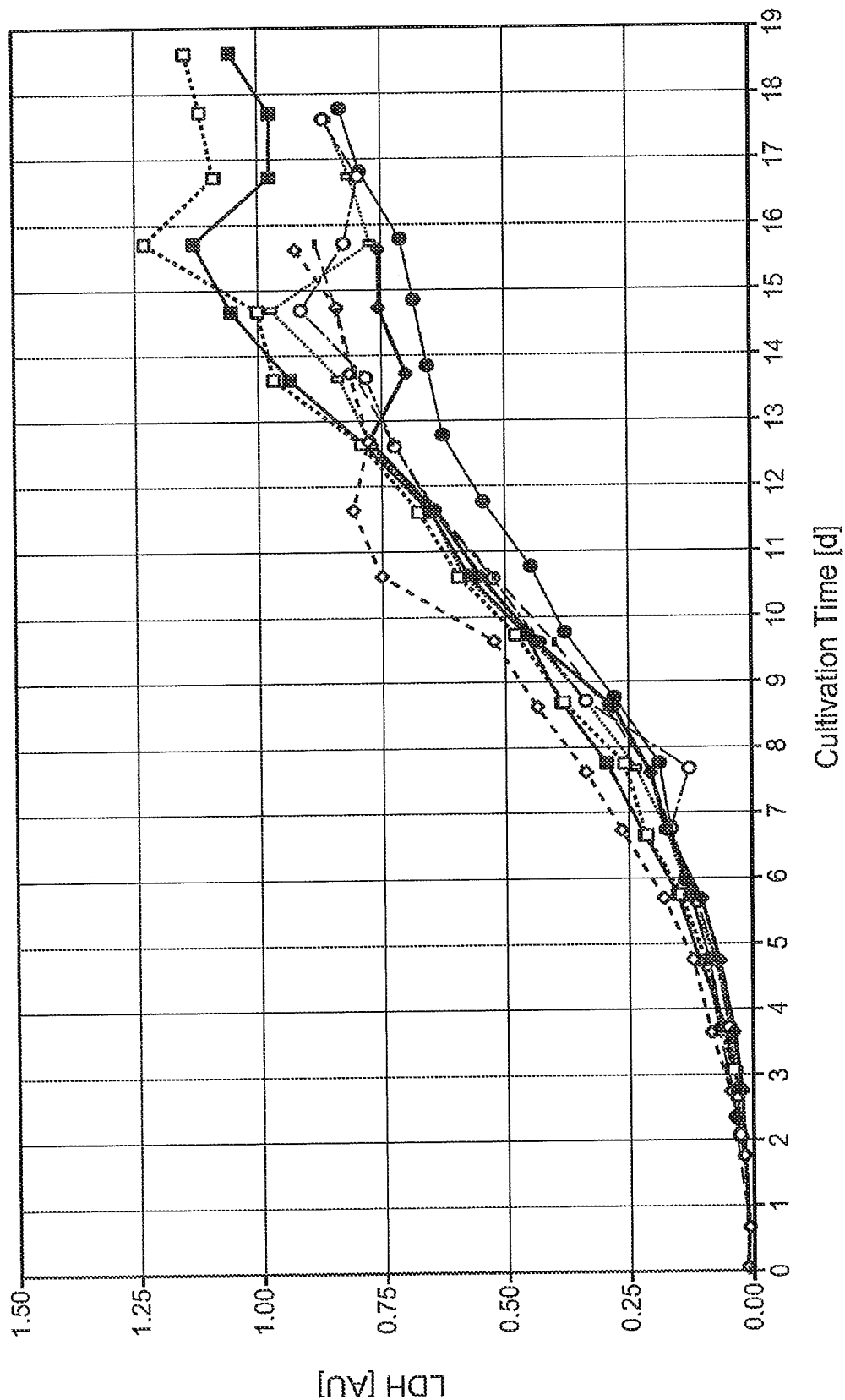

FIG. 27 shows the course of the LDH activity determined for different inoculation cell densities (ICD). 10,000 L process (black dashed line; inoculation cell density of 100%); 2 L fermentations (♦/ICD 100%); 2 L and 400 L fermentations (○/●/ICD 333%) and the 2 L cultivations (■/ICD 666%).

Figure 28:
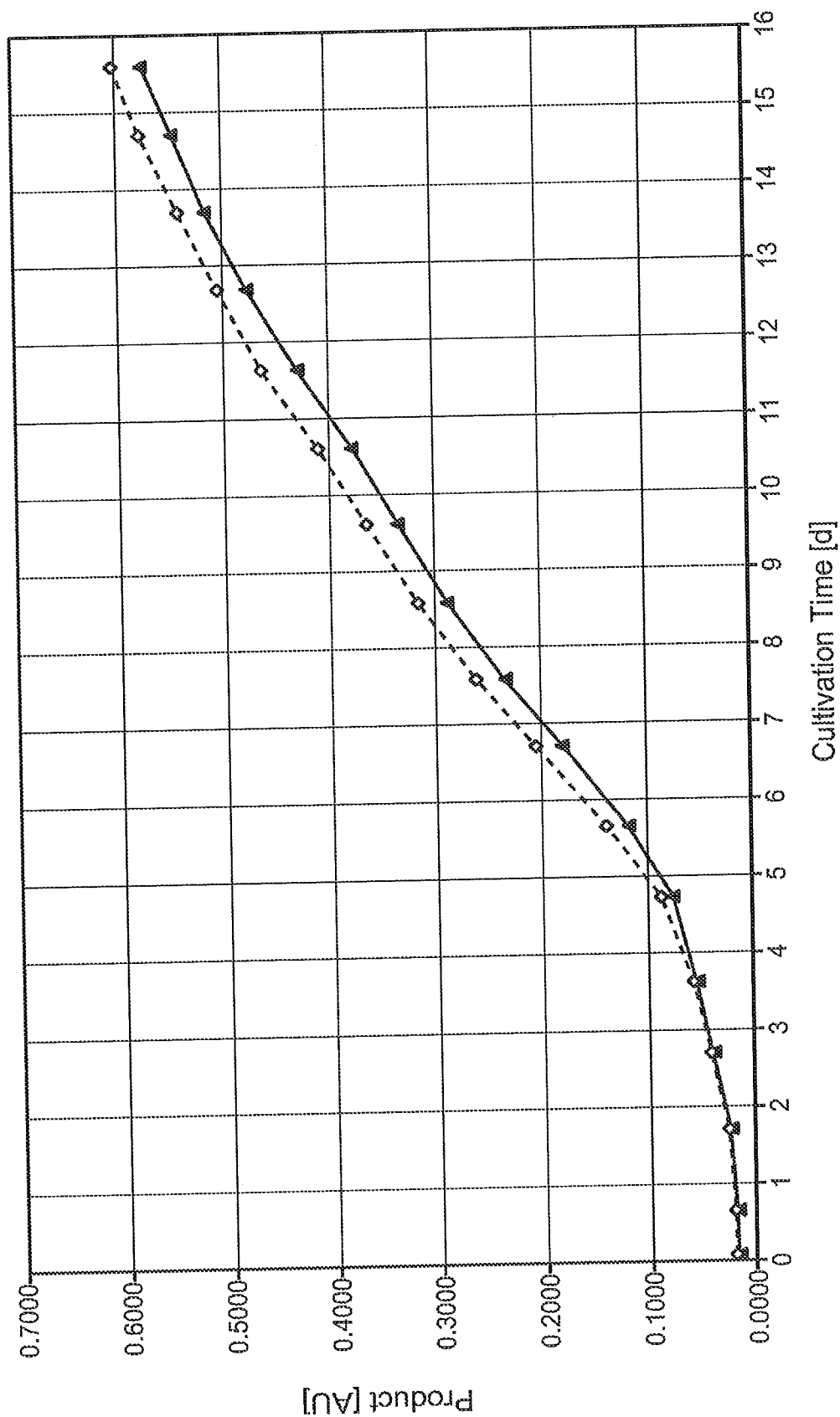

FIG. 28 shows antibody production for two 2 L fermentations (▲/▲) with inoculation cell density of 100%.

Figure 29:
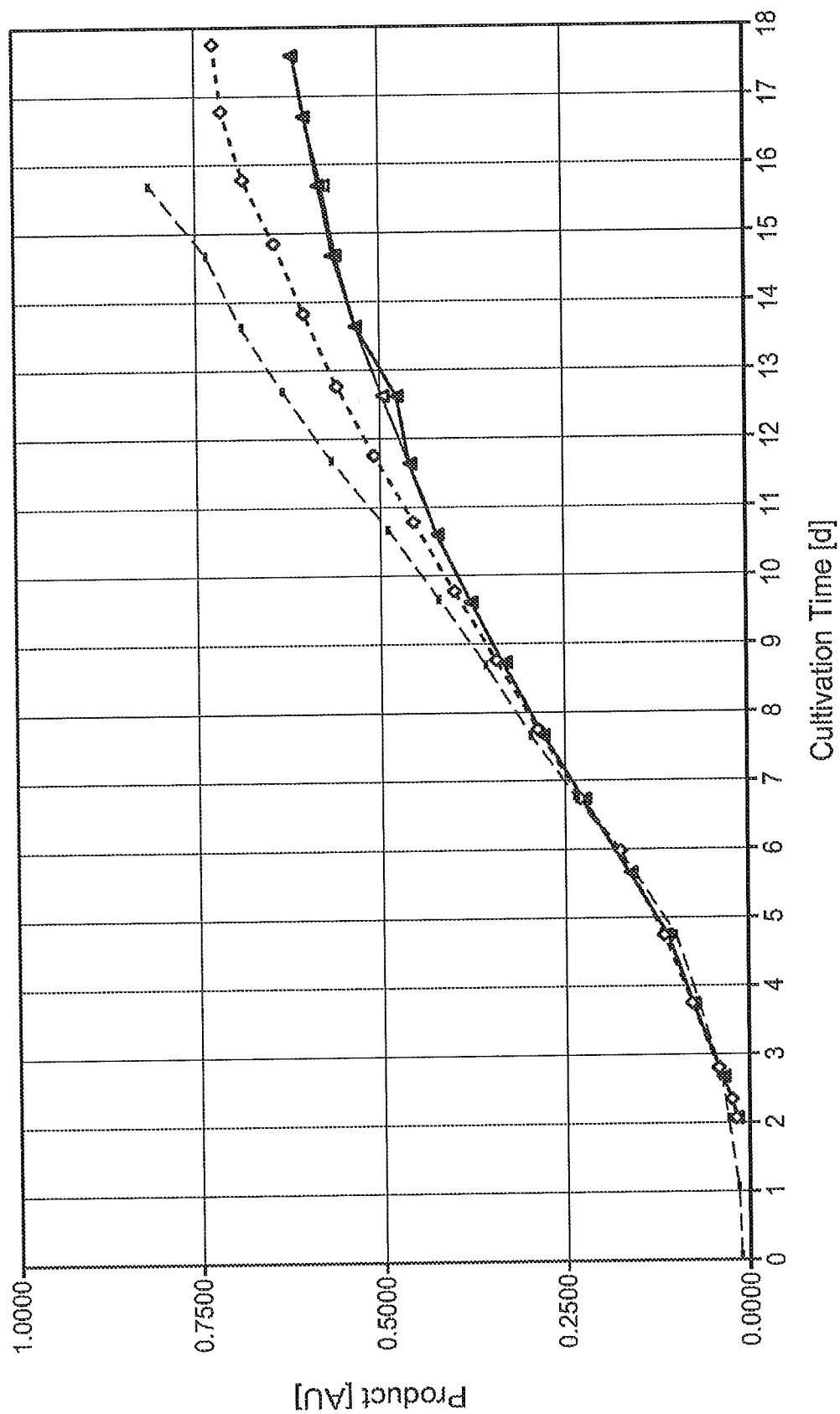

FIG. 29 shows antibody production for the 400 L bioreactor (♦) and the two 2 L controls (▲/Δ) with inoculation cell density of 333% compared to a 10,000 L process (black dashed line; inoculation cell density of 100%).

Figure 30:
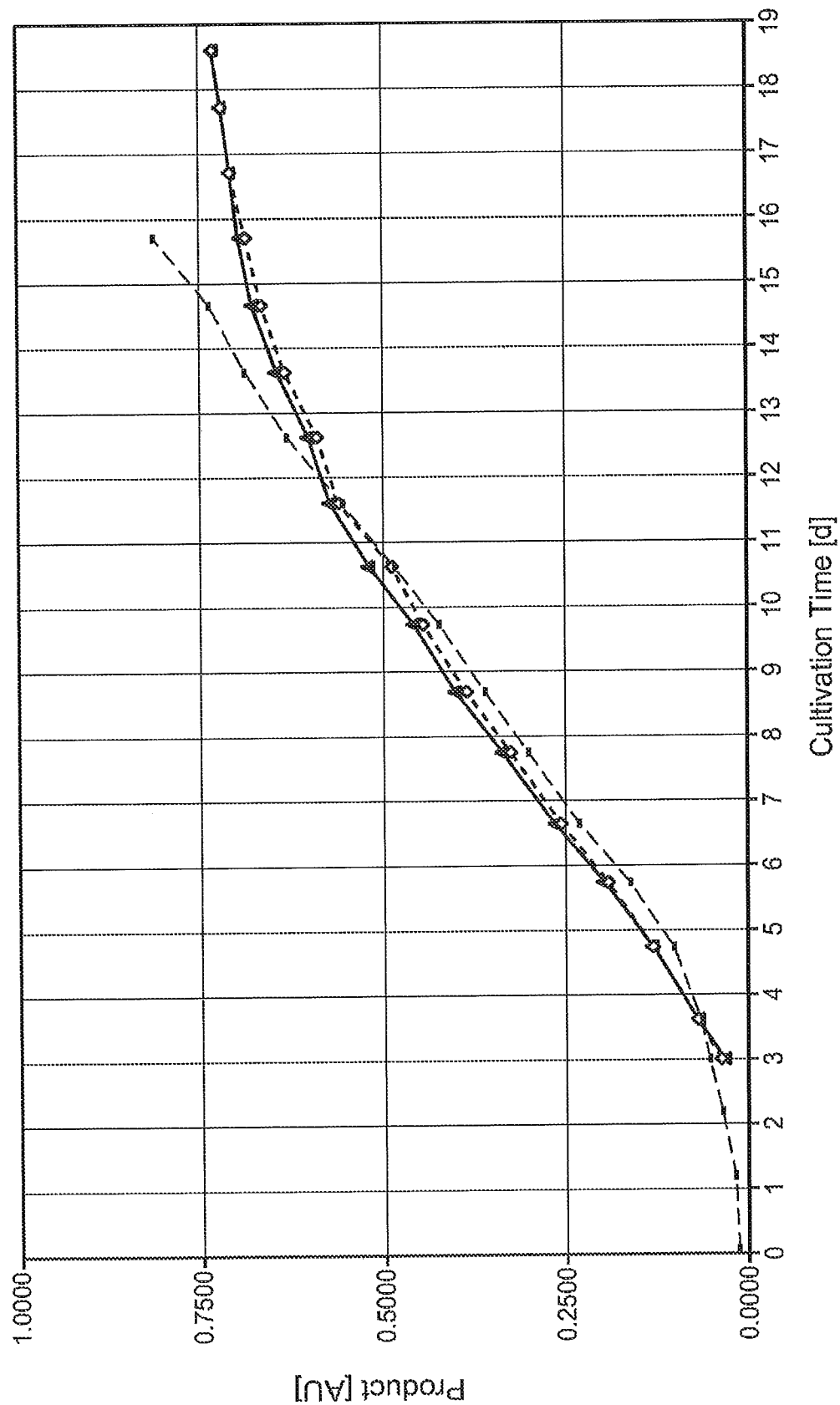

FIG. 30 shows antibody production for the two 2 L cultivations (▲/♦) with inoculation cell density of 666% compared to a 10,000 L process (black dashed line; inoculation cell density of 100%).

DESCRIPTION OF EMBODIMENTS

Figure 1:
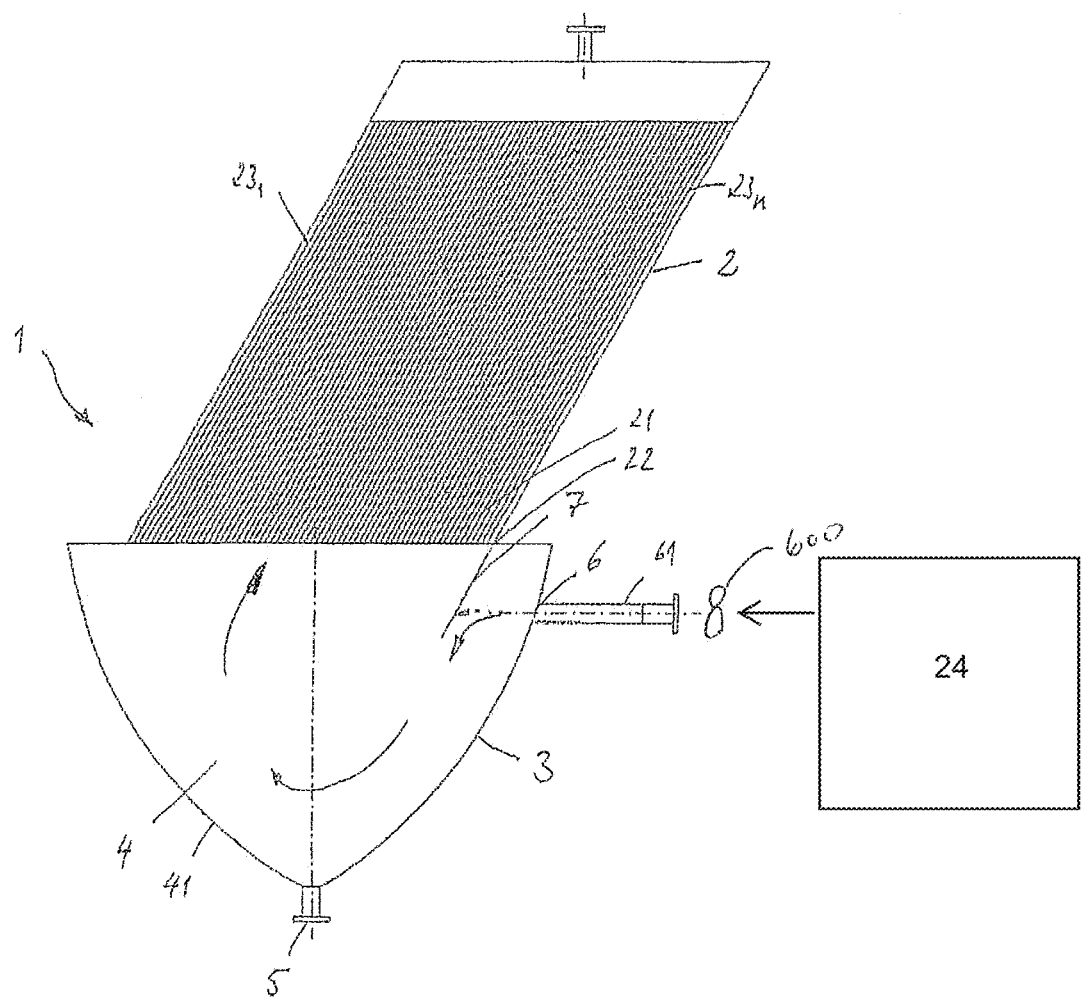
FIG. 1 shows a schematic cross sectional view of a separation apparatus according to a first embodiment of the invention.

FIG. 1 shows a separating apparatus 1 according to a first embodiment of the invention. The separating apparatus comprises a sedimentation settler 2 and a collection vessel 3. The collection vessel 3 is disposed underneath the sedimentation settler 2 and is also in fluid communication with the sedimentation settler 2. The collection vessel 3 forms a receiving chamber 4, and the receiving chamber 4 has an outlet 5 provided at its bottom. The plates of the sedimentation settler 2 do not extend into the collection vessel 3. Furthermore, the receiving chamber 4 has an inflow inlet opening 6. FIG. 1 also shows the inlet tube 61 through which liquid or fluid is guided into the collection vessel 3. The inflow inlet opening 6 is located at the upstanding side wall 41 of the collection vessel 3, for example a certain distance below the upper edge of the collection vessel 3. That is, the inflow inlet opening 6 is below the lower edge 22 of the sedimentation settler 2. The liquid or fluid in the present field is typically a suspension containing cells or cell lines. The suspension originates, for example, from a fermenter 24 and is supplied therefrom to the separation apparatus. Thus, the suspension supplied from the fermenter is introduced into the collection vessel underneath the sedimentation settler with a controlled downward direction, and then guided upwards to and through the sedimentation settler 2. The term "downward" denotes that the flow is in direction to the outlet of the collection vessel but not directly into the outlet of the collection vessel. The clear phase of the suspension is removed above the sedimentation settler, and the settled cells are removed at outlet 5.

As shown in FIG. 1, the collection vessel 3 may comprise an inflow deflection element 7. In more general terms, a deflection element 7 is arranged such that it is located within the collection vessel 3. The size of the collection vessel 3 and the deflection element 7 are adapted to each other such that the retention time of a fluid in the collection vessel 3 is reduced compared to a separating apparatus having a collection vessel without a deflection element. The deflection element is minimizing the direct interaction of inflowing particles, cells and/or fluids while enabling at the same time higher flow rates without negatively disturbing the fluid communication and/or the sedimentation of the particles, e.g. cells, which is necessary to reduce retention times. According to FIG. 1, the inflow deflection element 7 is located near or adjacent to the inlet opening 6. It is shaped and arranged such that it downwardly deflects an inflow of liquid or fluid through the inlet opening 6. This is shown in FIG. 1 by an arrow visualizing the curve of flow caused by the deflection element 7. As mentioned above, an inflow of liquid or fluid into the receiving chamber 4 will generally flow somewhat towards the bottom of the receiving chamber 4 due to gravity (shown in FIG. 1 by the dashed arrow). The deflection element 7, however, deflects the inflow in a controlled direction to the bottom of the collection vessel 3. In other words, the deflection element 7 impedes the liquid flow to flow along its natural path guided by gravity and controls that the stream of liquid change its direction downwardly.

The wall 41 of the receiving chamber 4 of FIG. 1 is curved like a cup or bowl, i.e. the upstanding wall is not flat but comprises a curvature such that the horizontal cross-sectional area decreases towards the bottom thereof. For example, the receiving chamber 4 has the shape of an inverse cone or truncated cone, or is cup-shaped or bowl-shaped, i.e. having a curved inner wall.

The arrangement and shape of the deflection element 7 and the curvature of the receiving chamber 4 are adapted to each other such that the initially downwardly deflected inflow is further guided up towards the sedimentation settler 2. This is also shown in FIG. 1 by the arrows exemplifying the flow of the fluid to reach the sedimentation settler 2. Thus, adjacent to the inlet opening 6, the inflow is first deflected downwardly. It is then guided by the inner wall 41 of the receiving chamber 4 further downwards and follows the generally curved shape of the vessel 3 and is the guided upwards and towards the sedimentation settler 2.

Figure 2:
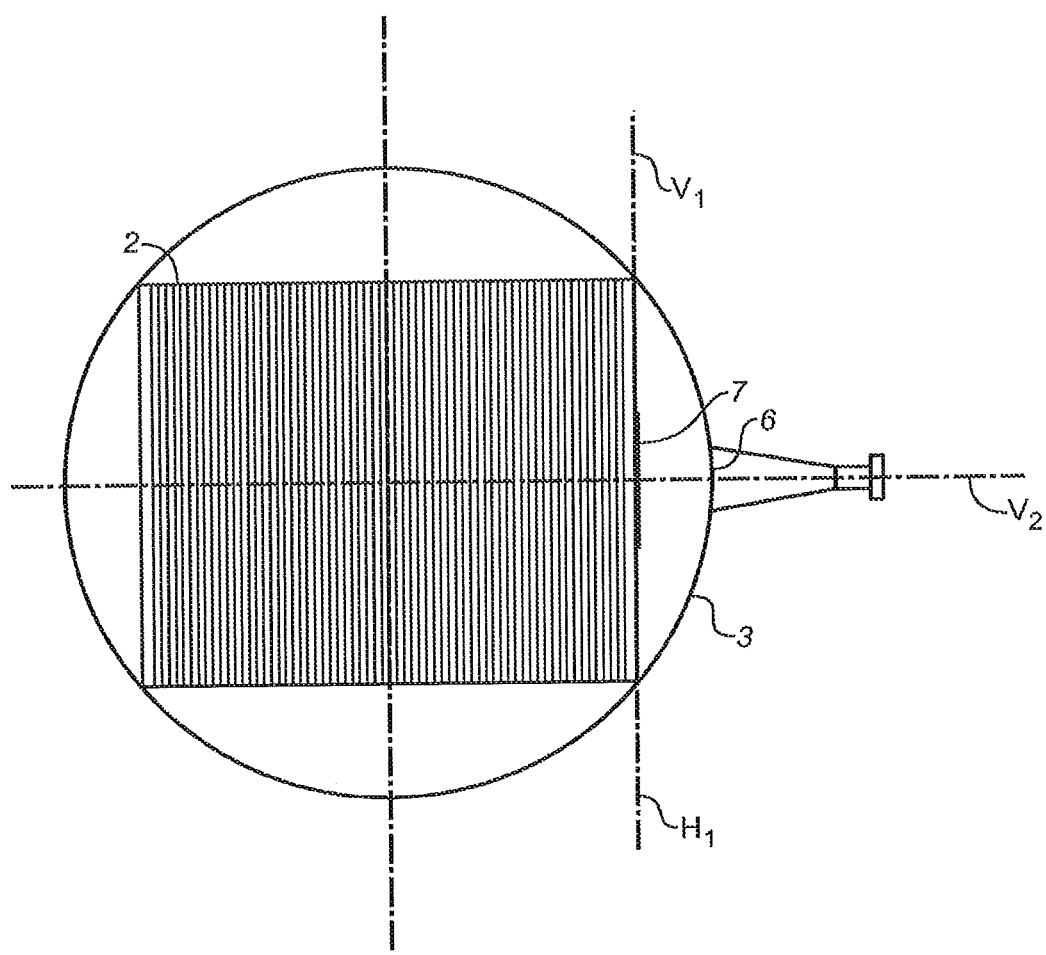
FIG. 2 shows a schematic cross-sectional top view of the embodiment of FIG. 1.
Figure 3:
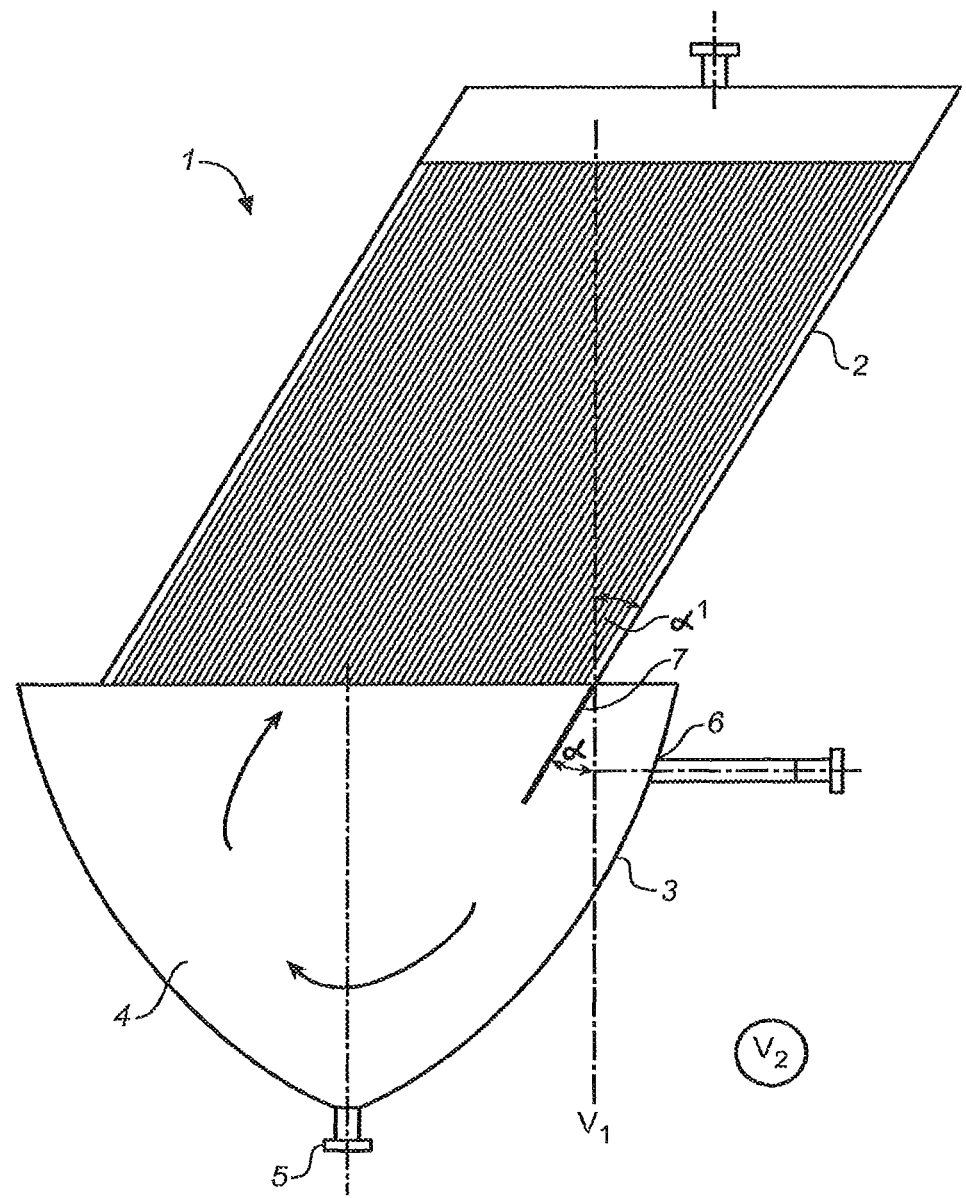
FIG. 3 shows the separation apparatus according to FIG. 1.

The inflow deflection element 7 may be a baffle plate. The baffle plate 7 is arranged inclined relative to a first imaginary vertical plane $V_1$ being perpendicular to a second imaginary vertical plane $V_2$ comprising the inflow direction axis through the inlet opening. This is shown in FIG. 3 which is identical to FIG. 1 except for the shown imaginary planes. In FIG. 3 the second imaginary vertical plane $V_2$ is the plane of the drawing. The first imaginary vertical plane $V_1$ is shown perpendicular to this plane $V_2$. In the shown embodiment, the baffle plate 7 is inclined under an angle α such that it intersects said first imaginary vertical plane $V_1$ along a horizontal line $H_1$. In FIG. 3 the horizontal line $H_1$ is also perpendicular to the second plane $V_2$. This can be seen in FIG. 2 which shows the horizontal line $H_1$ perpendicular to the second plane $V_2$ and also shows the upper edge of the deflection element 7. In the embodiment of FIGS. 1 and 3 the inclination α of the baffle plate 7 is the same as the inclination α' of the sedimentation settler 2 (see FIG. 3).

In this embodiment, the inflow inlet opening 6 is also located below the lower edge 22 of the sedimentation settler 2. In one preferred embodiment, a rotot (600) is provided upstream of the inlet opening (6) to set inflow in rotation. The rotor can include vanes.

Figure 6:
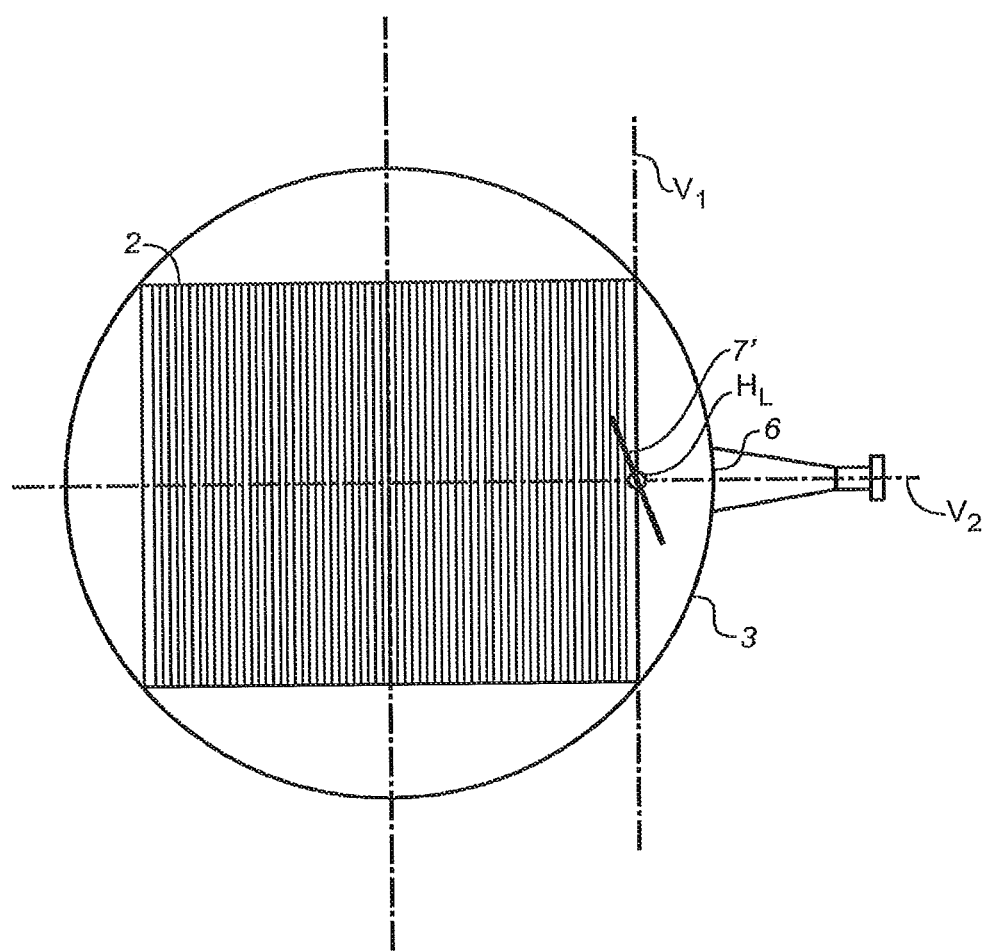
FIG. 6 shows a schematic cross-sectional top view of a separation apparatus according to a third embodiment of the invention.

In the alternative embodiment shown in FIG. 6, the deflection plate 7' is also arranged inclined relative to a first imaginary vertical plane $V_1$ being perpendicular to a second imaginary vertical plane $V_2$ comprising the inflow direction axis through the inlet opening. However, in this embodiment, the deflection plate is inclined such that it intersects said secondary imaginary vertical plane $V_2$ along a horizontal line $H_2$.

In the embodiment of FIG. 1, the baffle plate 7 extends in elongation of the lower end 21 of the sedimentation settler 2. In particular, it extends into the receiving chamber 4 at that lower edge 22 of the sedimentation settler 2 being closest to the inlet opening 6. Thus, it can be said the deflection element forms an extension of the outer surface of the sedimentation settler reaching into the collection vessel.

Figure 5:
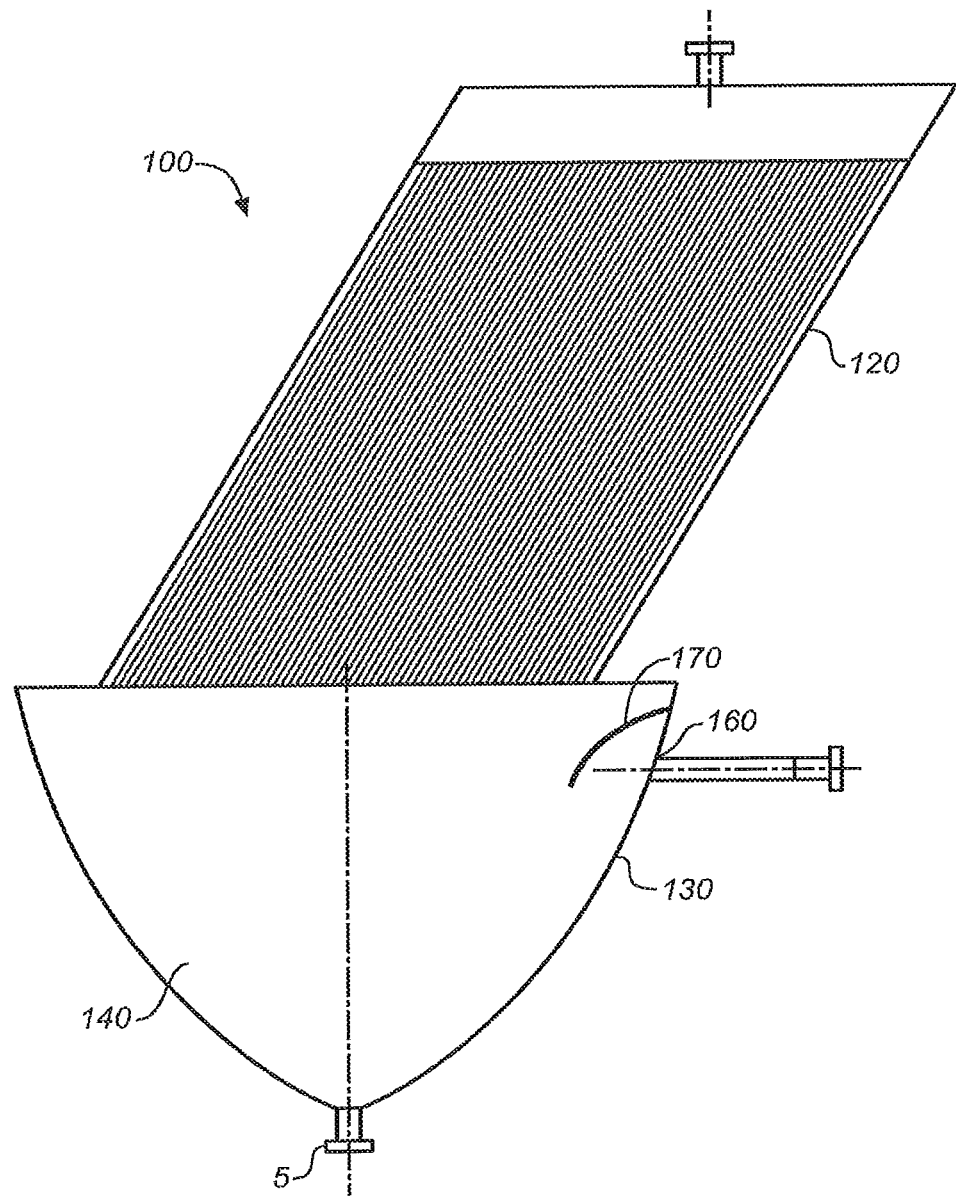
FIG. 5 shows a schematic cross sectional view of a separation apparatus according to a second embodiment of the invention.

Alternatively, the baffle plate 170 is connected to the inner wall of the collection vessel 130 above the inlet opening 160. Such an embodiment is shown in FIG. 5. In FIG. 5, a curved deflection plate 170 is shown but it may as well be straight as long as it is inclined relative to the horizontal. Also in this embodiment, the inflow inlet opening 6 is located below the lower edge of the sedimentation settler 2.

Figure 8:
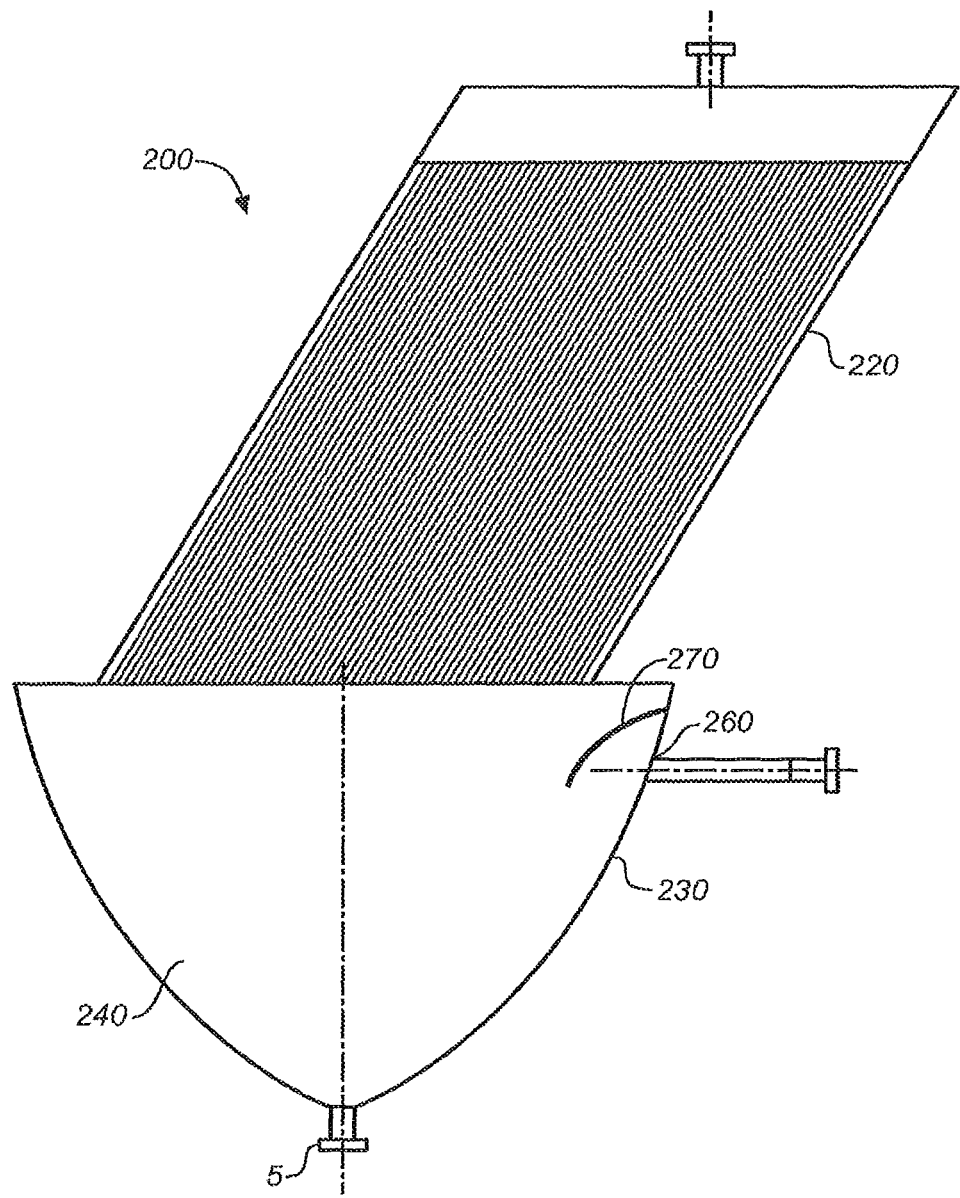
FIG. 8 shows a schematic cross sectional view of a separation apparatus according to a third embodiment of the invention.

Alternatively, the baffle plate 270 is connected to the inner wall of the collection vessel 230 directly above the inlet opening 260, i.e. the baffle plate is an extension of the upper half of the inlet 261. Such an embodiment is shown in FIG. 8. In FIG. 8, a curved deflection plate 270 is shown but it may as well be straight as long as it is inclined relative to the horizontal.

In any of the embodiments of the invention, the deflection element extends into the receiving chamber to an extent that it extends downwardly beyond the inflow direction axis through the inlet opening. More preferably, the deflection element extends into the receiving chamber to an extent that it extends downwardly beyond the lower edge 22 of the inlet opening to ensure that the inflow of liquid reaches the deflection element and cannot flow substantially horizontally, thus, simply passing the deflection element.

The vertical height of the collection vessel 3 is preferably in the range from 400 mm to 500 mm, more preferably about 450 mm. Its maximum or top diameter may range from 600 mm to 700 mm, preferably about 650 mm. The horizontal centerline or inflow direction axis of the inlet opening is preferably located about 80 mm to 90 mm underneath the upper edge of the collection vessel, more preferably about 88 mm. The length of the baffle plate is preferably in the range from 150 mm to 200 mm, more preferably about 180 mm. The horizontal width of the baffle plate is at least the same as the width of the projected flow leaving the inlet opening at the location of the baffle plate, or larger.

The settler plate length may be within a range from 600 to 900 mm, preferably within 700 to 800 mm, and is more preferably about 720 mm. The settler plate width may be between 400 mm and 500 mm, and is preferably about 430 mm. The inclination of the settler may be 15 to 60°, preferably 30-45°, and more preferably 30°.

The defection plate may have a width of 450-200 mm, preferably about 430 mm at its lower end and about 215 mm at its upper end. The height of the deflection plate may be between 130 mm to 200 mm, and is preferably about 130 mm.

The inlet opening may have an oval shape with diameters of preferably about 80-90 mm (preferably about 85 mm) and 12 to 20 mm (preferably about 17 mm).

According to a further embodiment, the separating apparatus 1 may comprise a means for controlling the direction and reducing the velocity of the inflow upstream of the inlet opening 6, or within the inlet tube 61. The means can be for example a flow distributer or any reducer of flow velocities known to a person skilled in the art. The means reduces the negative acceleration when the cells impinge on the deflection plate, and supports a flow of the cell suspension along the container walls (similar to the flow according to the embodiment shown in FIG. 6, described below).

The sedimentation settler 2 comprises a plurality of plates 23 forming a plurality sedimentation channels in between. The sedimentation settler preferably has from 60 to 70 channels, preferably 65 or 66 channels.

Figure 4:
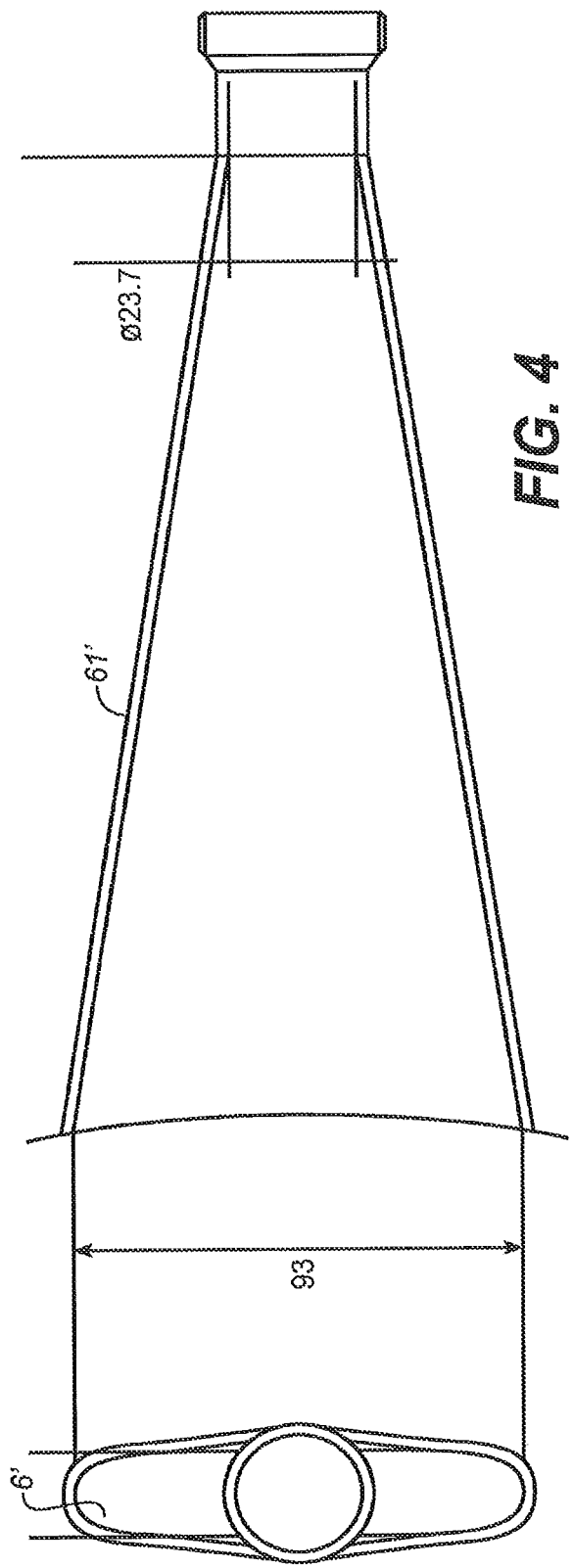
FIG. 4 shows a preferred shape of the inlet opening of the separation apparatus.

FIG. 4 shows an embodiment of the inlet opening 6'. As can be seen in FIG. 4, the inlet opening has a non-circular shape, preferably the shape of an oval. FIG. 4 is a schematic top view so that the inlet opening extends along the circumference of the collection vessel. Such non-circular inlet opening causes a relaxation of the inflow so that the flow speed is decreased. Furthermore, with such inlet opening the liquid inflow provides that the whole width of the baffle plate is used to deflect the flow downwards. The flow cross section is widened by such inlet opening.

Figure 7:
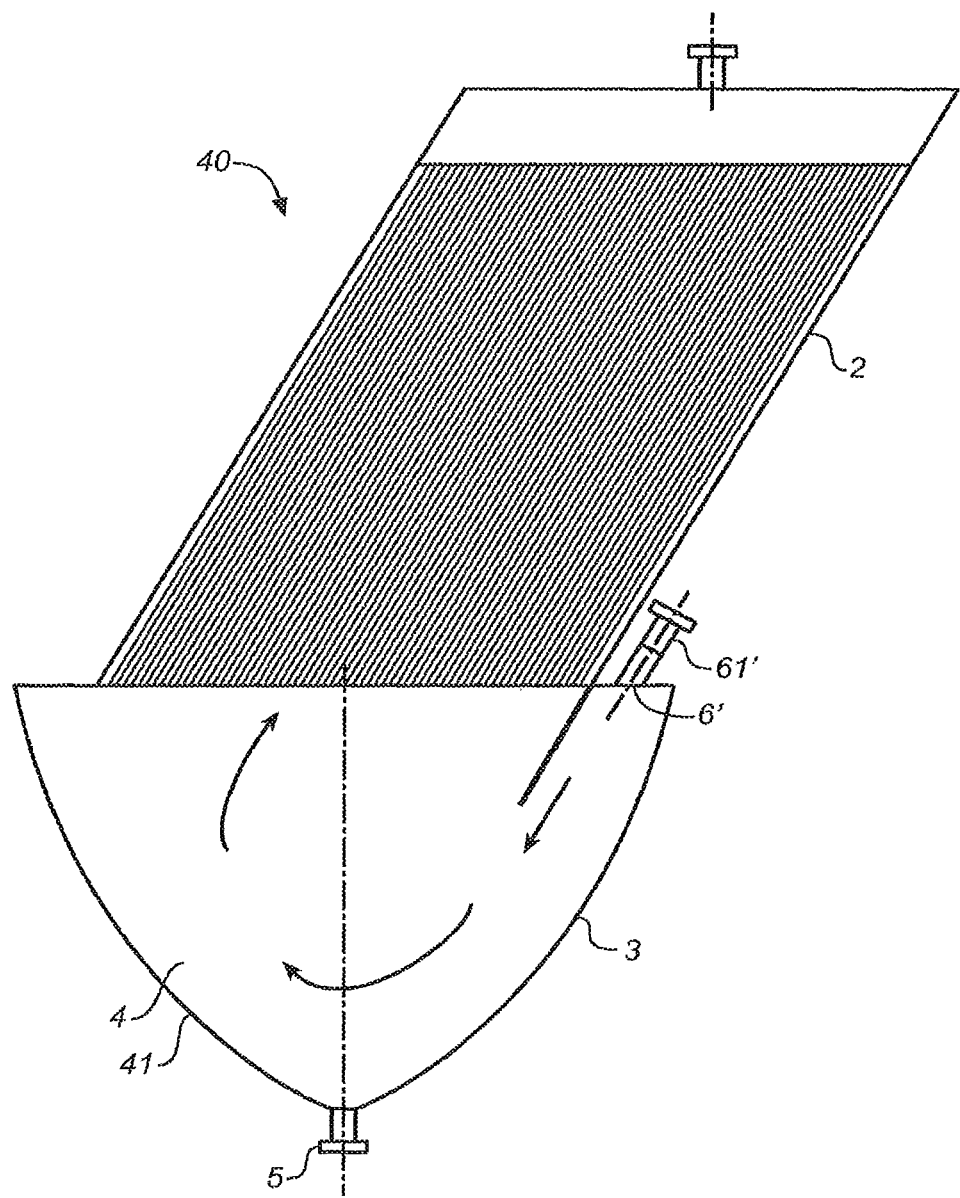
FIG. 7 shows a schematic cross sectional view of a separation apparatus according to the second aspect of the invention.

FIG. 7 shows a schematic cross sectional view of a separation apparatus 10 according to the second embodiment of the invention. In FIG. 7, in comparison to FIG. 1, same components of the separation apparatus are denoted with the same reference numerals.

In this embodiment, the inflow inlet opening 6 is located at the same vertical height level of the separating apparatus as the lower edge of the sedimentation settler 2.

In this embodiment of the invention, the inflow inlet opening 6', i.e. the inflow tube 61', is arranged such that the direction of fluid inflow through the inlet opening 6' is parallel to the direction or inclination (a') of the sedimentation settler 2.

Alternatively, the inflow inlet opening is not strictly parallel to the direction of the channels of the sedimentation settler 2, but deviates from the direction/inclination of the sedimentation settler by +/−10°, if seen in a imaginary vertical plane ($V_2$) comprising the inflow direction axis through the inlet opening 6'.

Thus, this arrangement of the inflow tube 61' guides the inflow in a direction to the bottom of the collection vessel 3. The arrangement and location of the inflow tube 61' and inlet opening 6' and the curvature of the receiving chamber 4 are adapted to each other such that the initially downwardly deflected inflow is further guided up towards the sedimentation settler 2. This is also shown in FIG. 7 by the arrows exemplifying the flow of the fluid to reach the sedimentation settler 2. Thus, inflow is initially directed downwards. It is then guided by the inner wall 41 of the receiving chamber 4 further downwards and follows the generally curved shape of the vessel 3 and is then guided upwards and towards the sedimentation settler 2. Nevertheless, a deflection element according to the first embodiment (e.g., as shown in FIG. 3) can be added to the second embodiment to further guide the flow along the desired direction.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

Furthermore, in the claims the word "comprising" does not exclude other elements or steps, and the indefinite article "a" or "an" does not exclude a plurality. A single unit may fulfill the functions of several features recited in the claims. The terms "essentially", "about", "approximately" and the like in connection with an attribute or a value particularly also define exactly the attribute or exactly the value, respectively. Any reference signs in the claims should not be construed as limiting the scope.

The following represents non-limiting examples of the invention and its practical uses.

Example 1: Material and Methods of the Following Exemplified Cell Cultivations and Cell Separations 1.1 Cell Line The cell line used in the examples was a recombinant CHO DG44 cell line producing a therapeutic antibody of human IgG class.

1.2 Buffer/Media

For prevention of foam Antifoam Dow Emulsion; Biesterfeld Spezialchemie GmbH was used. To regulate the pH 1 mol/L sodium carbonate was employed.

1.3 Cultivation 1.3.1 Experimental System

Figure 9:
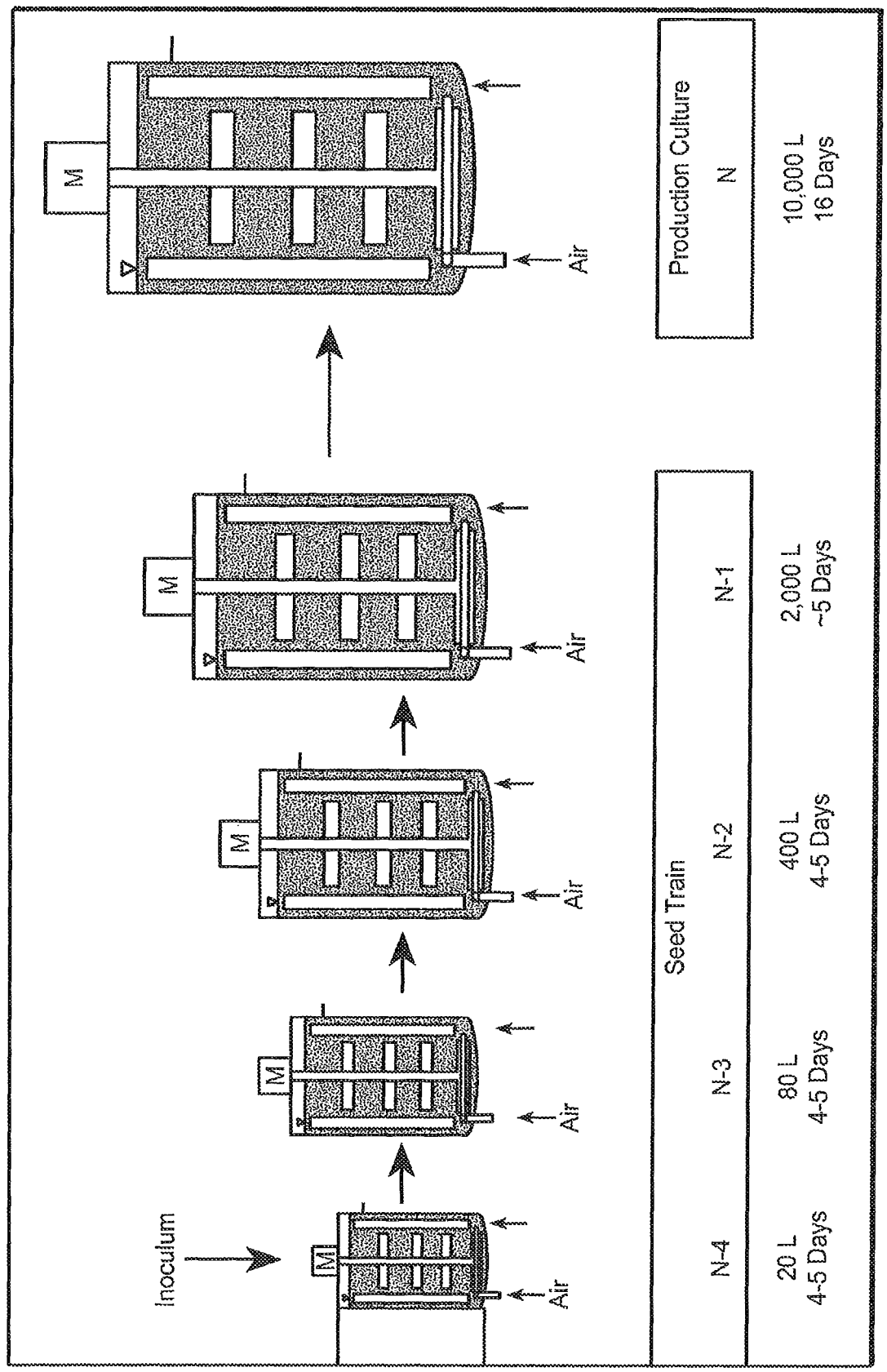
FIG. 9 shows a standard seed train and main fermentation process.

The CHO cell line (see above) was cultivated in a fed batch cultivation. The seed train started with an inoculation from shaking flasks and comprised four consecutive seed train cultivations each consecutive cultivation with increased cultivation volume (20 L to 3,000 L) and a 10,0000 L main fermentation (see FIG. 9).

The temperature is automatically regulated by a double heating jacket in all cultivations. PH regulation is made by the addition of an alkaline solution (base) with peristaltic pumps as well as by the introduction of gaseous $CO_2$ via mass flows. Dissolved oxygen is automatically regulated by air and nitrogen, as well as the pressure and the stirring velocity.

1.3.2 Inoculation Culture

The cultivation takes place in shaking flasks with a step-wise volume expansion up to 2 L. The cultivation parameters were about 37° C., gassing with air and 5% $CO_2$ at relative humidity of ≥70%. As shaking rate 125 rpm was used. Upon reaching the desired cell density in the 2 L-flasks the 20 L-bioreactor was inoculated.

1.3.3 Seed Train to 400 L

The N−4 step (20 L) was performed with selective pressure and 3% reactor volume (RV) feed per day. In the N−3 to N−1 steps the cells were grown without selective pressure and also 3% RV feed per day. The temperature was regulated at 37° C. The pH value was regulated at about pH 7. The $pO_2$ was regulated at about 30% by using pressurized air. Samples during the seed train (step N−4 to N−2) were taken daily and cell concentration, pH, $pCO_2$, osmolality and product concentration were determined. For Analytical methods see example 1.4.

A production process starting at small scale comprising seed and inoculum train was performed. At the n−1 scale (see e.g. FIG. 10) the routinely used batch operation was replaced by the large scale perfusion to generate high cell densities in order to achieve higher inoculation cell densities of the production bioreactor N. The established process using non perfusion mode leading to lower inoculation cell densities in production scale was compared to the modified process using the perfusion element leading to higher cell densities. Details of the results, operations and comparison of the process are shown below using the separation apparatus described before 1.3.4 Perfusion Process at 3,000 L Scale The N−1 step was performed as perfusion cultivation with the object to reach higher cell densities in 5 days of perfusion compared to a process without perfusion cultivation (see e.g. FIG. 10).

Up to the N−2 step the seed train was performed according to the established process. Modifications were introduced only in the N−1 cultivation.

The entire perfusion system consisted of an 3,000 L bioreactor, the separation apparatus as reported herein with vibrator and connected spiral cross flow heat exchanger, three peristaltic pumps (Watson Marlow Inc.) for feed addition (model 624Di), perfundate drain (model 624Di) and circulation (model 620U), two medium tanks (each with 3,000 L volume) for the perfusion medium and the waste (perfundate). Sample devices were at the perfundate line and at the bioreactor.

The separation apparatus was used to separate the cells from the culture supernatant and recycle viable cells back to the bioreactor.

Figure 10:
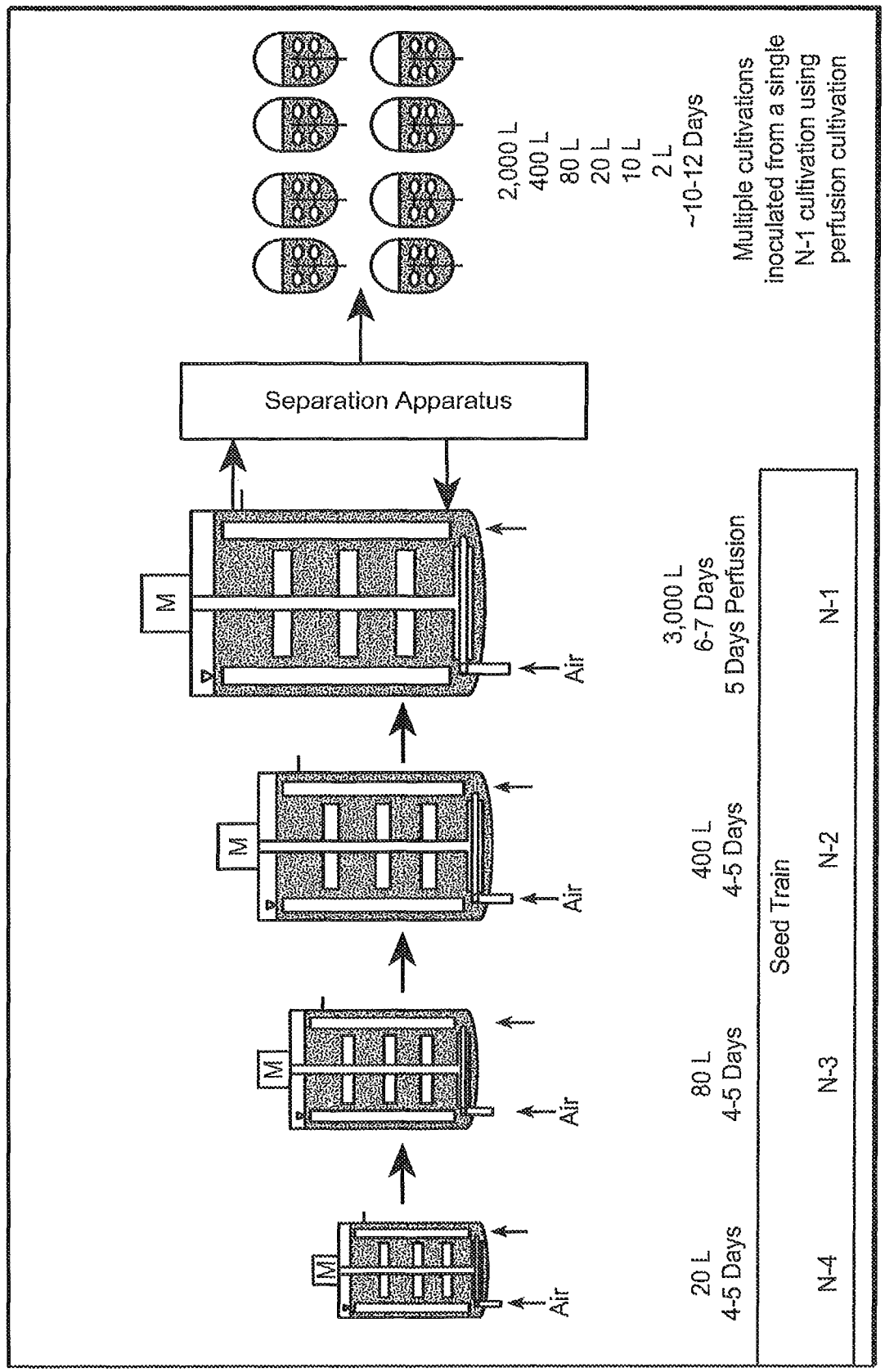
FIG. 10 shows schematic sketch of modified seed train with the separation apparatus employed in the (N−1) fermentation and parallel inoculation of a multiple parallel fermentation at different scale.

Two consecutive perfusion fermentations with five days of perfusion each were realized. The second perfusion fermentation was inoculated by a split of the first 3,000 L operation at a seeding density of four times that of the first bioreactor with simultaneous inoculation of the production bioreactors (FIG. 10).

The cells were first grown in batch mode for one to two days, and then perfusion was started as outlined above for the first perfusion operation. During the perfusion samples from the bioreactor and the perfundate were taken in the beginning every three hours. After the second day samples were taken every six hours but the feed volume flow was regulated every three hours.

During the production cultivation samples were also taken every day.

1.3.5 Cultivations at Variable Cultivation Volume

The inoculation from the N−1 seed train cultivation of the thereafter following bioreactor was performed in systems of different scale (2 L up to 400 L) with different parameters (see Table 1), such as different cell densities which are the major target of this experiments. Other parameters where adapted to the increased cell densities. One condition is representing the established reference process with lower cell densities compared to the herein reported perfusion mode. The cells do not show any lag phase or limitations after inoculation at higher cell densities. Therewith the total fermentation time (seed train and main cultivation) can be decreased whereby equal yields can be achieved in a single batch.

Different parameters were used to determine, if the available higher inoculation cell densities available by using a perfusion cultivation influence cell growth or quality.

The medium and feeds were the same in all cultivations. The time schedule of the individual events during the cultivation, e.g. the starting time of the feed, was adjusted according to the cultivation volume and starting cell density based on the reference production process. For example time points were shifted to an earlier point if the inoculation cell density had been increased compared to a process without settler/perfusion (reference process).

The temperature was regulated at about 37° C. during the growth phase, the pH value was regulated at about pH 7 and the $pO_2$ was set to 30% using pressurized air.

TABLE 1

Overview of cultivations

| Nr | volume | inoculation cell density [%] |
|---|---|---|
| 1 | 400 L | 333 |
| 2 | 80 L | 666 |
| 3 | 2 × 2 L (reference) | 100 |
| 4 | 2 × 2 L | 333 |
| 5 | 2 × 2 L | 666 |
| 6 | 1 × 2 L | 666 |

TABLE 1-continued

Overview of cultivations

| Nr | volume | inoculation cell density [%] |
|---|---|---|
| 7 | 1 × 2 L | 333 |
| 8 | 10 L | 666 |
| 9 | 10 L | 666 |

1.4 Analytical Methods 1.4.1 Cell Density

Cell densities were determined by trypan blue method using a CEDEX HiRes automated cell counter (Roche Innovatis, Bielefeld) as per manufacturer's instructions. The cell culture fluids were diluted 1:5 with PBS-puffer by reaching a cell density over 16 times the standard inoculation density. The ratio of viable cells against all measured cells showed the viability.

1.4.2 Substrate Concentrations

Concentration of glucose, lactate, glutamine and ammonium in the culture were determined using a BIOPROFILE flex analyzer (Nova Biomedicals, Waltham). The measure method is based on biosensors or ion-selective electrodes.

1.4.3 pH- and $pCO_2$-Measurement

The pH value in the bioreactor was daily controlled externally by a pH-meter (WTW, Inolab). The $pCO_2$ value was checked daily per an AVL Compact 3 blood gas analyzer (Roche, Switzerland)

1.4.4 Osmolality

To check the osmotic pressure during the perfusion and the changed feed the osmolality were measured daily. An Osmomat 030 (Gonotec, Berlin, Germany) was used. The measuring technique is based on comparative measurements of the freezing points of pure water and of solutions. Whereas water has a freezing point of 0° C., a solution with saline concentration of 1 mOsmol/kg has a freezing point of −1.858° C.

1.4.5 Lactate Dehydrogenase Activity

The lactate dehydrogenase activity (LDH) is related to the cell exposure during the fermentation. Damaged cells deliver more LDH to the medium than viable cells. The measurement technique is based on an enzymatic assay on micro titer plates. With attendance of LDH NADH will be oxidized to $NAD^+$ and pyruvate will be reduced to lactate. The velocity of NADH decrement is measured by an extinction of 340 nm.

1.5 Antibody Analyses

Antibody titers were quantified by high performance liquid chromatography (HPLC) using a Poros A affinity column.

Example 2: Seed Train Cultivation 1.1 Seed Train Up to 400 L

This was carried out as outlined in Example 1. Once an inoculation cell density was reached, the feed in 20 L to 400 L bioreactor started with defined volume flow rate. The 20 L bioreactor was splitted once, and the 80 L bioreactor inoculated twice for back-up intention.

1.2 Design of the Separation Apparatus

Due to the large scale of the separation apparatus an adequate heat exchanger had also to be constructed to cool the culture prior to application to the apparatus. To reduce the stress and pressure on the cells a spiral cross flow heat exchanger was used (MCE AG, Germany).

Internally, the settler consisted of 65 removable plates of stainless steel. The total settle area was set to of from 7 $m^2$ or 10 $m^2$, e.g. 8 $m^2$. The settler was inclined at an angle of 60° from the horizontal. The inclination can be changed by a rotation wheel if required. An electromagnetic vibrator was attached, which was activated automatically for 10-20 s every 15 min. The angular adjustment and the vibration interval ensured that the cells were recycled efficiently.

Prior to use the whole equipment was sanitized or rather sterilized (CIP and SIP) and tested for absence of microorganisms. The qualification of the design (DQ), the installation (IQ) the following qualification of the operation (OQ) and performance (PQ) of the equipment corresponding to the standard operation procedure and sterility test showed no abnormality.

1.3 Perfusion 1.3.1 Procedure

In order to start the perfusion of the culture, the cell culture fluid of the bioreactor was pumped through a dip tube to the heat exchanger, which cooled the culture to 10-15° C. This served as a slow down of the cell metabolism during the time outside of the bioreactor, i.e. under non-controlled conditions.

The circulation pump controlled the flow rate of the culture with a volume flow rate of about 390 L/h constantly. Total loop volume was about 200 L. The perfusion feed rate was regulated by the cell density in the bioreactor.

1.3.2 Cell Growth

Figure 11:
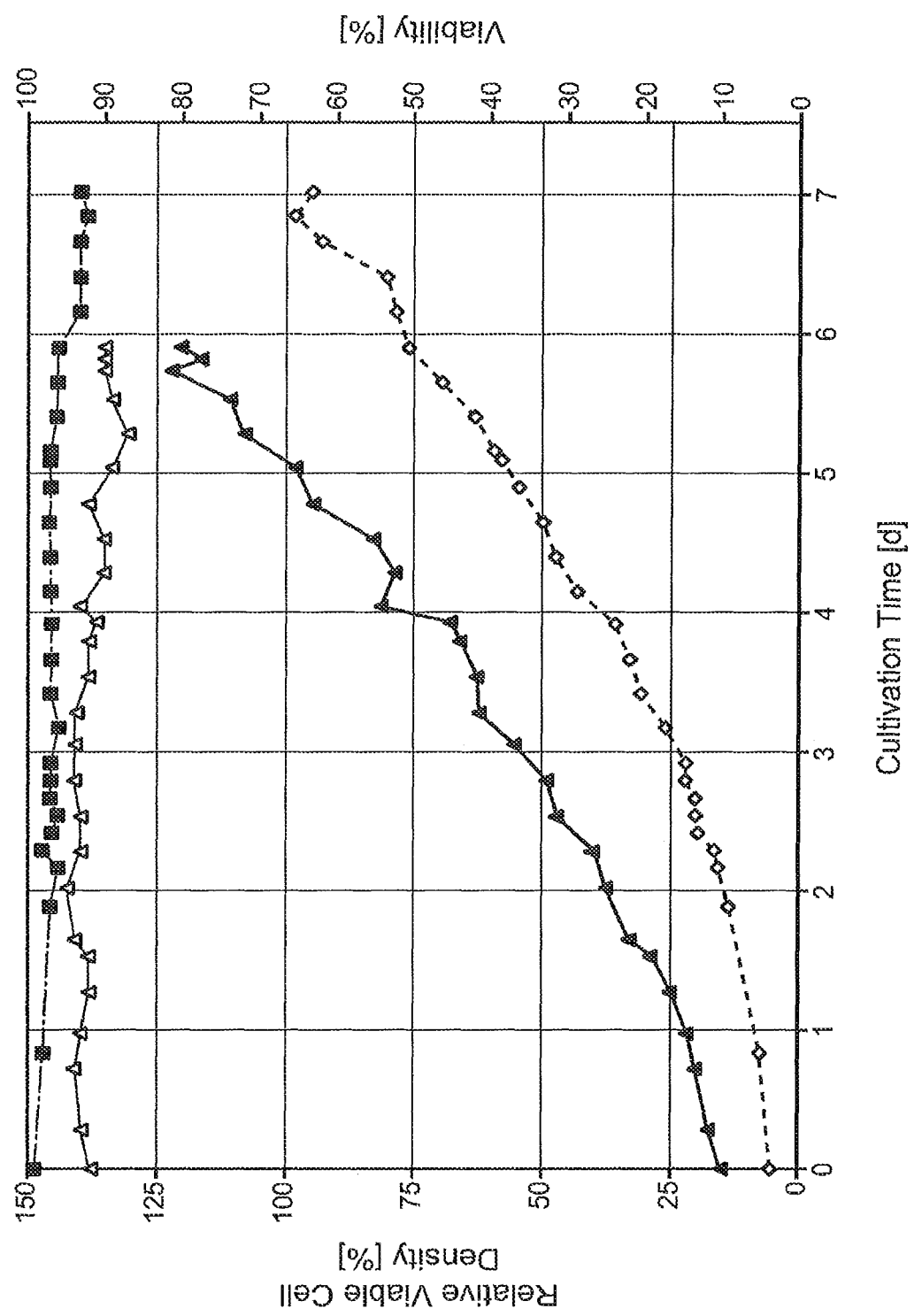
FIG. 11 shows viable cell density and viability profile of the perfusion runs P1 (♦) and P2 (▲).

Comparison of viable cell density (VCD) and cell viability over the course of two consecutive perfusions (P1 and P2) are shown in FIG. 11. A cell density of more than 100% (about 130%) was reached in both cases. An undercut of the viability of <85% has not happened.

1.3.3 Cell Retention (Grade/Efficiency)

Figure 12:
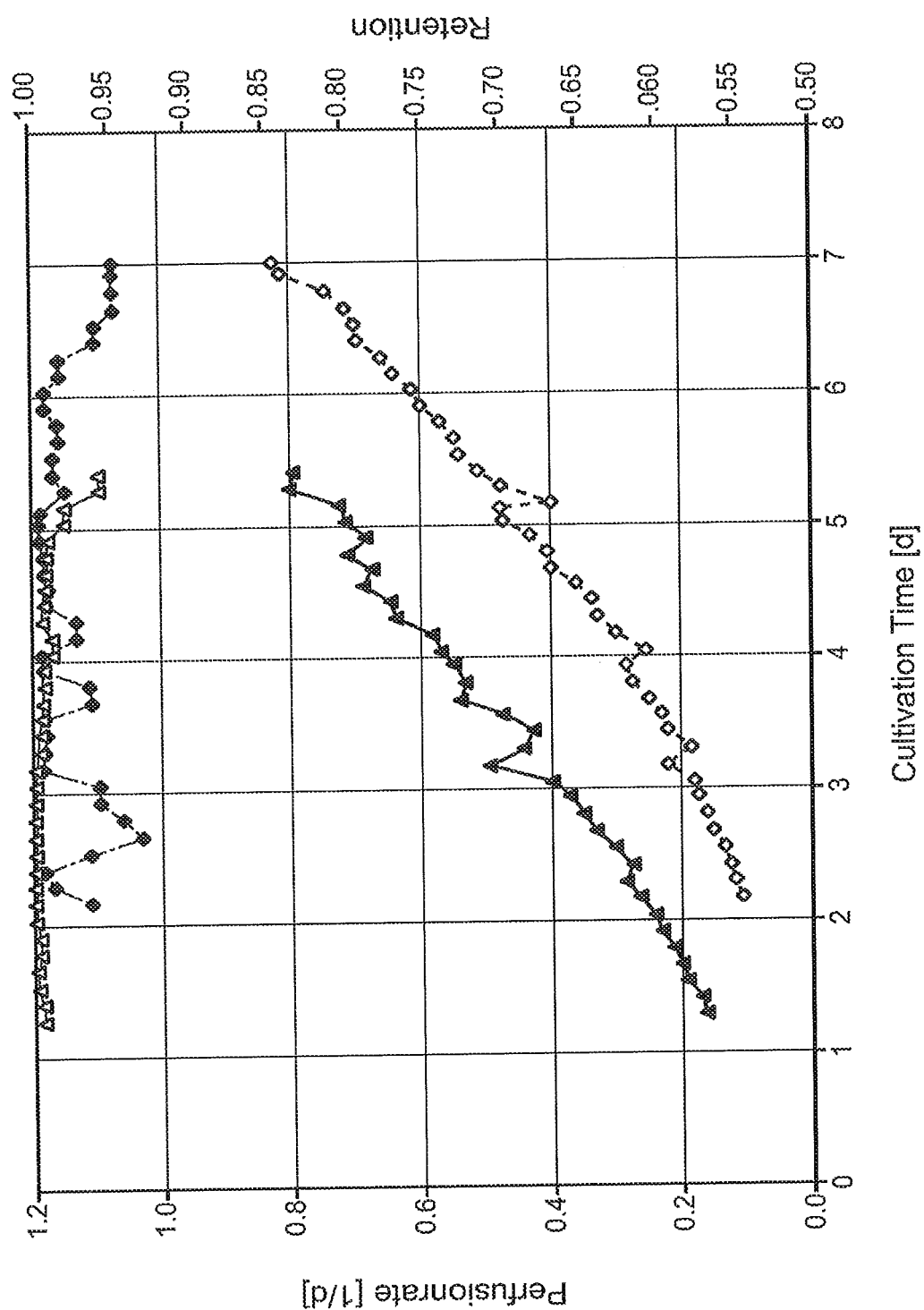
FIG. 12 shows perfusion feed volume per day (perfusion rate) and retention level of the two perfusion runs P1 (♦) and P2 (▲).

As outlined herein, the separation apparatus functioned well in separating the cells from the supernatant. The separation efficiency and perfusion volumes are shown in FIG. 12. The separation efficiency (retention level) was ≥0.9=90% over the whole time. Once the retention declined to <95% the vibration time was extended.

A maximum perfusion feed turnover of 0.9 times bioreactor volumes or 2,400 L/d (corresponding to 3,000 L for the whole system minor 200 L fluid in the circulation) was sufficient to support cell growth. Separation efficiencies for both perfusions remained above 95%. These results were obtained without optimization of the perfusion by adjustment of the settler angle or the pumps.

As can be seen from FIG. 12 both perfusion runs show comparable cell retention of at least 95% (upper part of FIG. 12) and a comparable increase in the perfusion rate. It has to be kept in mind that P1 started the perfusion after two days of fed-batch whereas P2 started the perfusion after only one day of fed-batch. Thus, the curves for P2 start earlier than those for P1.

An optimization of the perfusion rate can be realized by adjustment of the settler angle for better cell reflux or by feed optimization for higher cell densities.

1.4 Cultivation 1.4.1 Cell Growth and Viabilities

Exemplary the fermentations Nr. 1, 3, 4 and 5 (see Table 1 above) are compared to a production cultivation.

The fermentations were inoculated with different cell densities. The feed start time were adjusted correspondingly. To obtain a comparable product concentration in comparison to the 10,000 L cultivation (run 3 with 2 L volume with an inoculation cell density of 100%) in a shorter time the inoculation cell densities were raised to 333% (runs 1 and 4 with 400 L volume and 2 L volume, respectively) and 666% (run 5 with 2 L volume). Two fermentations with an inoculation cell density of 100% were also performed as a control for the production process.

The perfusion employed in the N−1 fermentation of the seed train does not influence cell growth of the cells in the thereafter following fermentations, i.e. no lag phase was identifiable.

Figure 13:
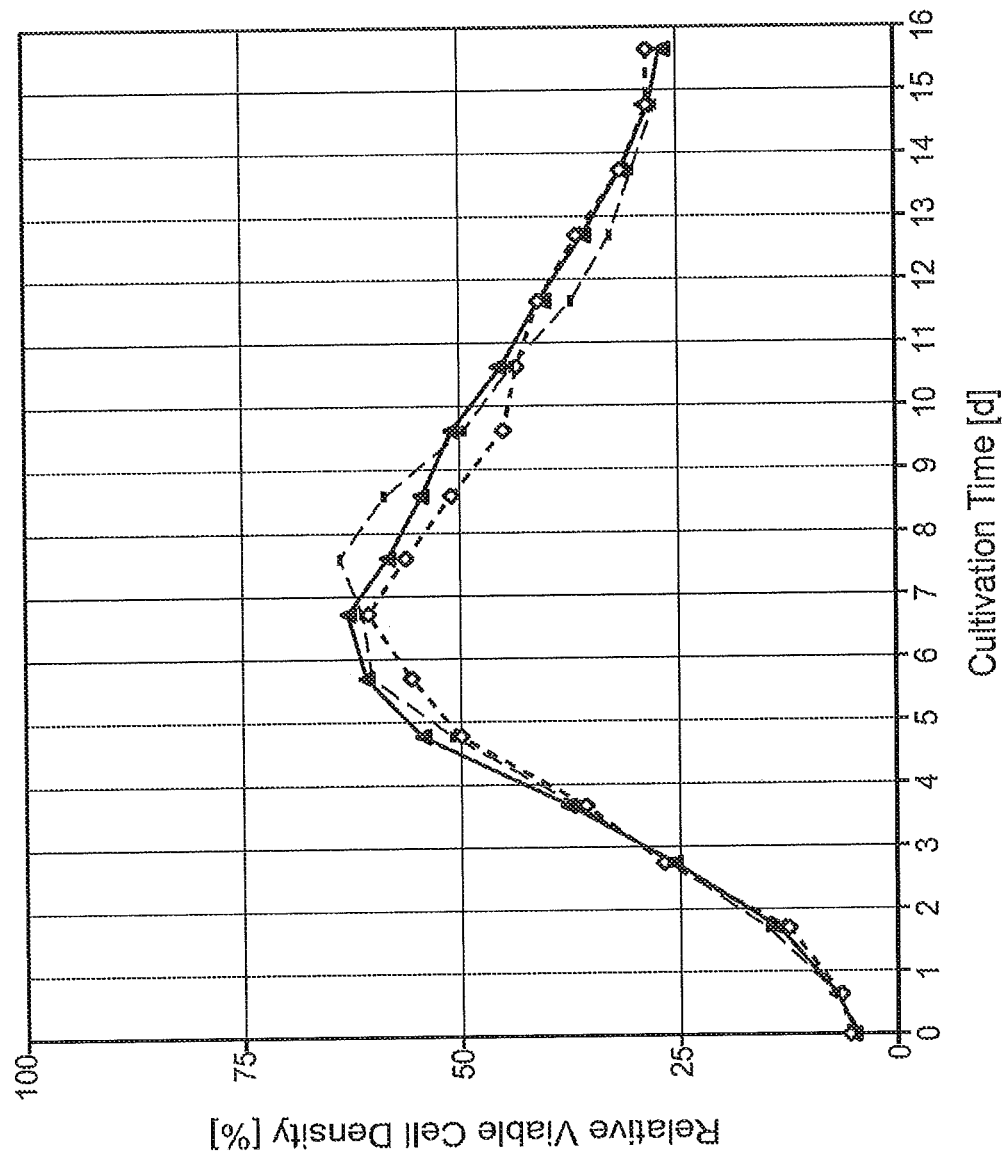
FIG. 13 shows the course of the viable cell density of two 2 L cultivations (♦/▲) compared to a 10,000 L process (shown as black dashed line).

FIG. 13 shows the cell growth of the 2 L cultivations in comparison to the average of a 10,000 L fermentation.

Figure 14:
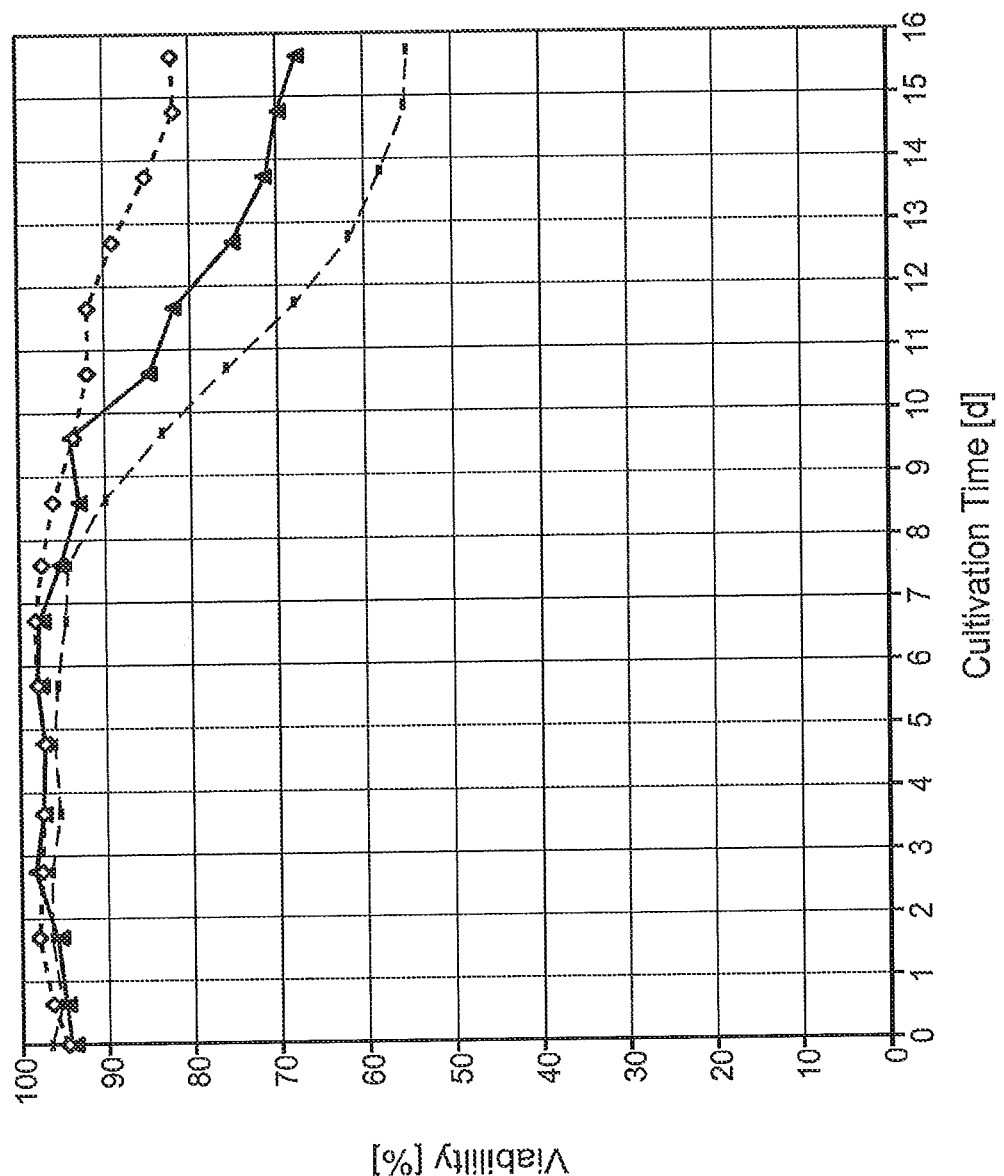
FIG. 14 shows the course of the viability of two 2 L cultivations (♦/▲) compared to a 10,000 L process (shown as black dashed line).

A comparison of established production process to the higher inoculation cell densities derived from the settler operation was performed (see FIG. 14). No differences in viability, cell growth, metabolism of the cells was observed. The perfusion had no influence on growth and viability of the cells.

Figure 15:
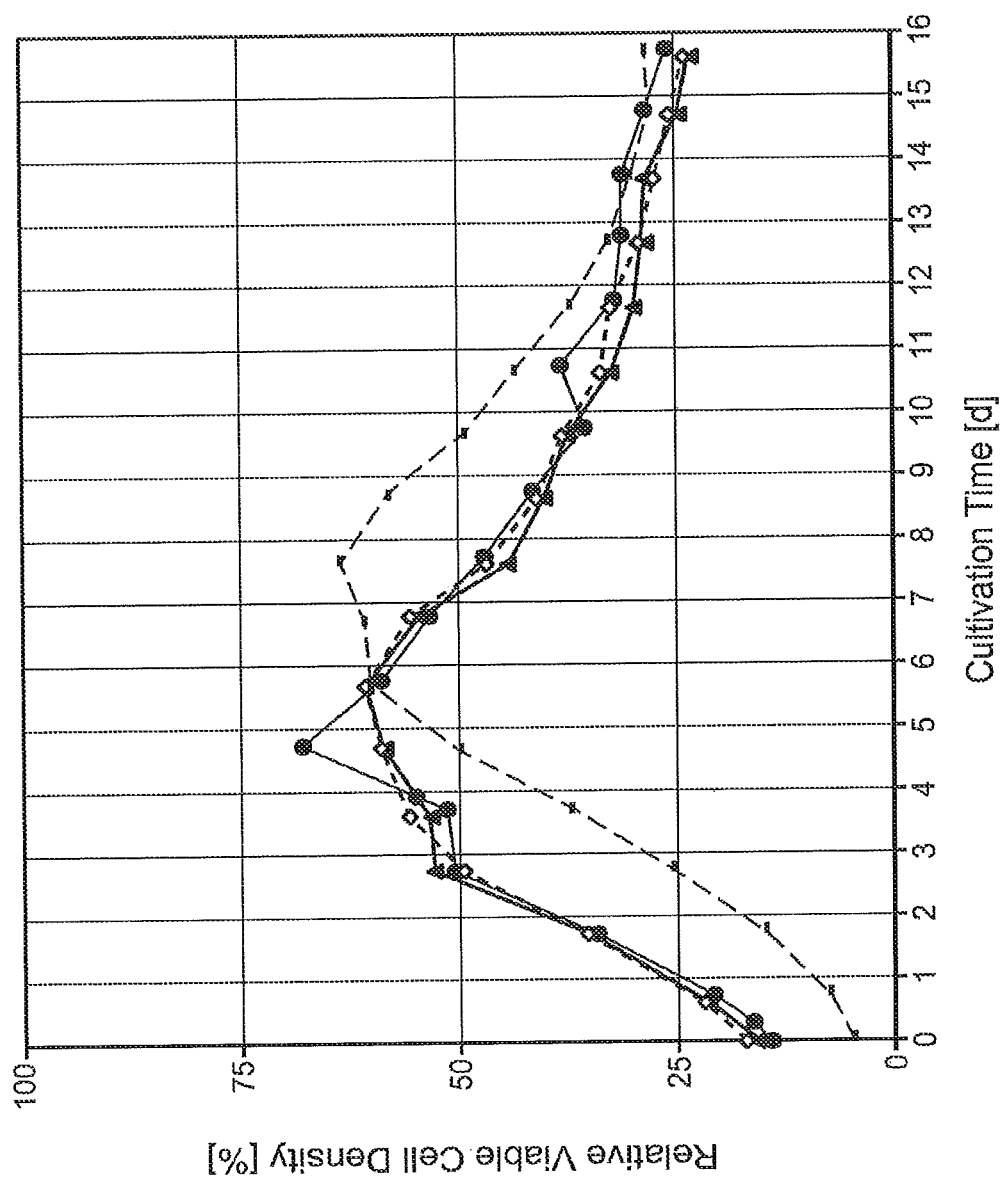
FIG. 15 shows the course of the viable cell density of cultivations starting at an inoculation cell density of 333%: viable cell density of the 400 L bioreactor and the two 2 L cultivations (♦/▲) compared to a 10,000 L process (black dashed line; inoculation cell density of 100%).
Figure 16:
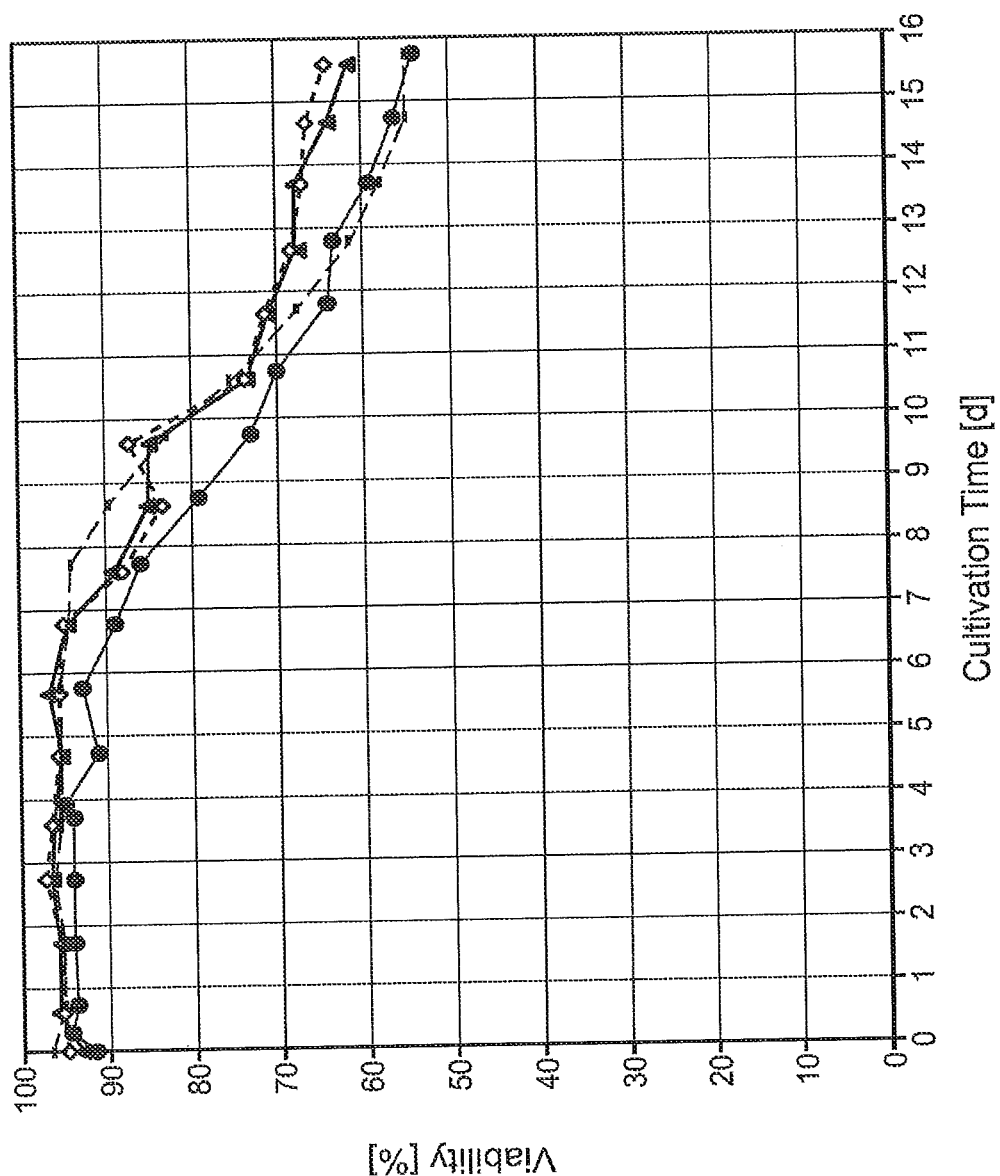
FIG. 16 shows the course of the viability of cultivations starting at an inoculation cell density of 333%: Viability of the 400 L bioreactor and the two 2 L controls (♦/▲) compared to a 10,000 L process (black dashed line; inoculation cell density of 100%).

FIGS. 15/16 show the viable cell densities and viabilities of three fermentations (1×400 L and 2×2 L) with an inoculation cell density of 333% in comparison to a reference production process (dashed lines). The higher inoculation cell density shortened the cultivation time by about 2 days as the maximum cell densities were reached already at about day 5 at a volume of 400 L and a volume of 2 L compared to day 7 at a volume of the production process Also the higher inoculation cell density did not lead to a lag phase during exponential cell growth.

Figure 17:
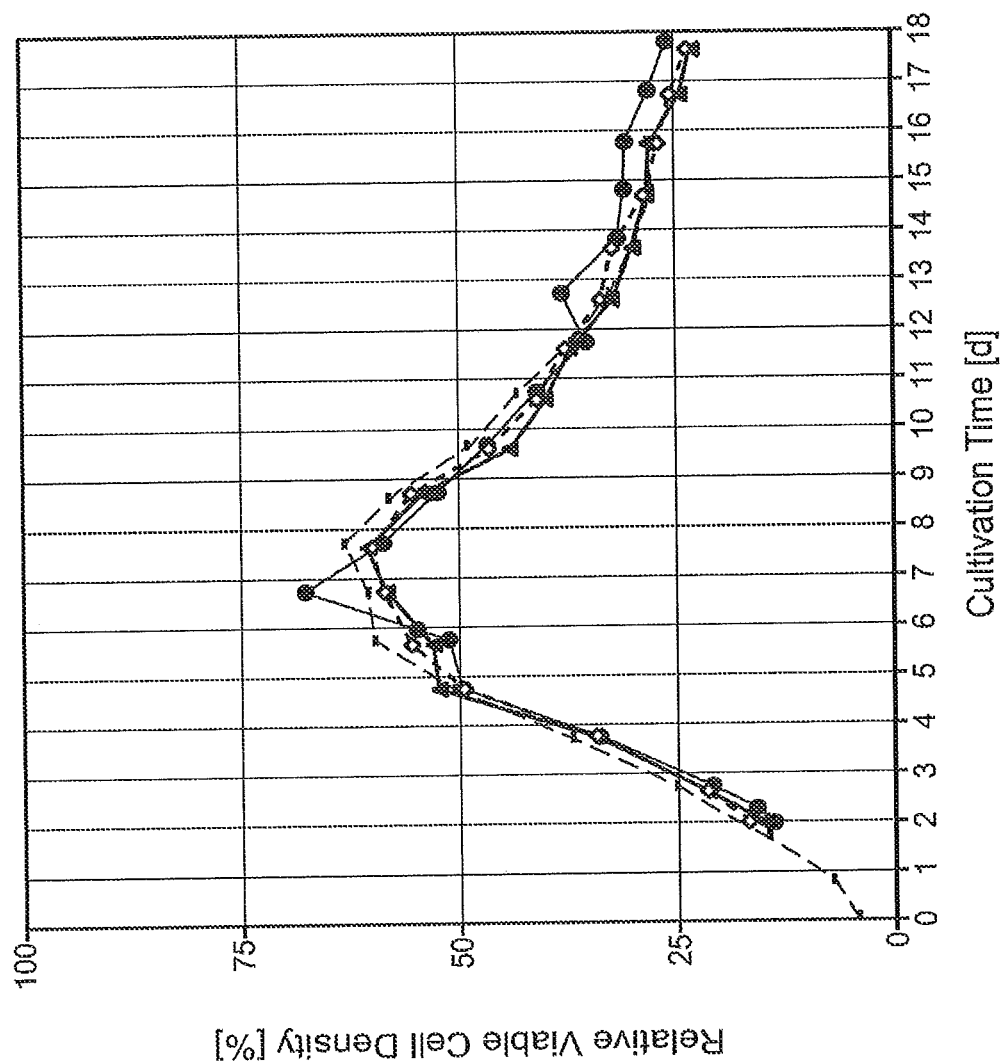
FIG. 17 shows curves of FIG. 15 shifted about +2 days along the x-axis.
Figure 18:
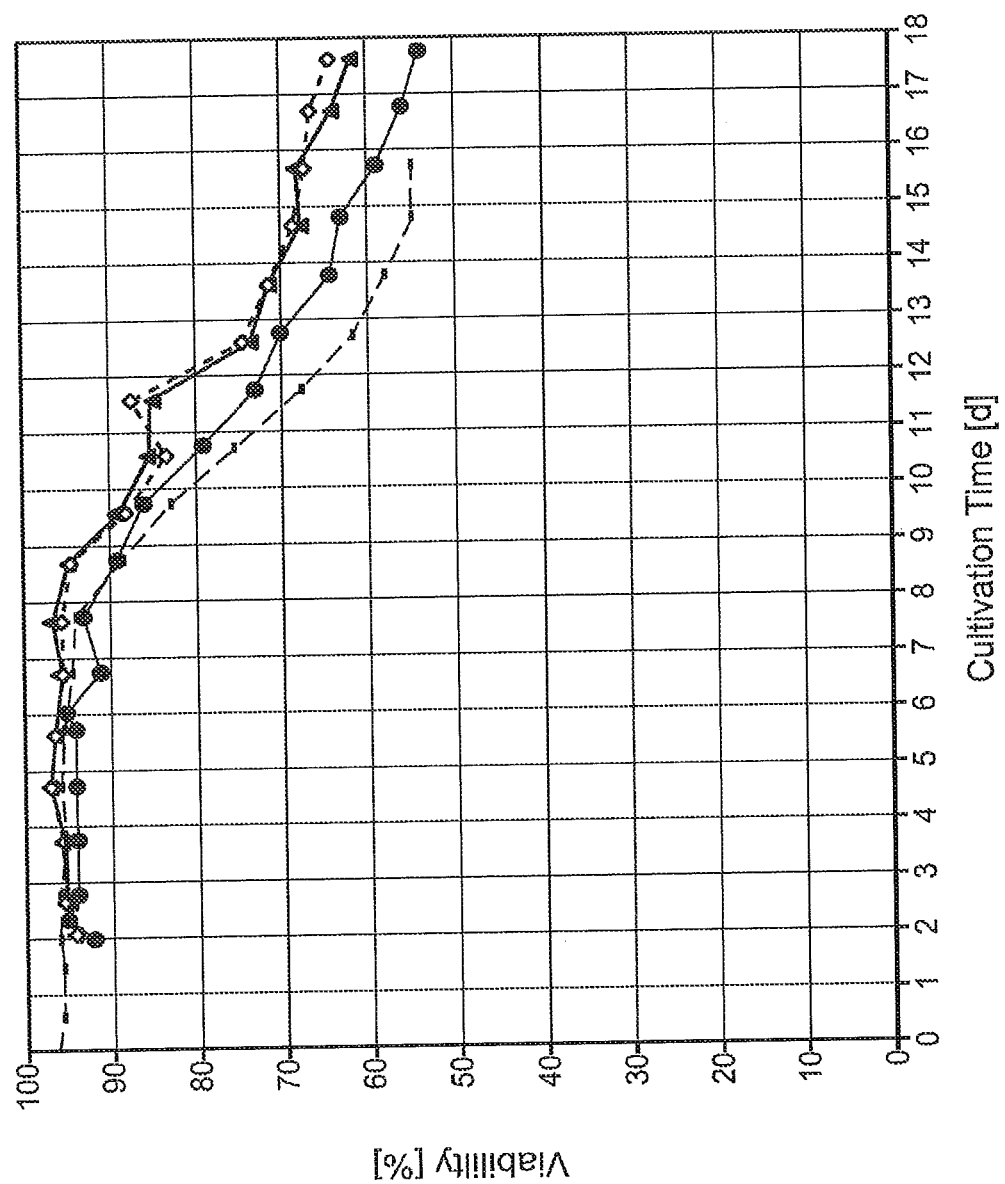
FIG. 18 shows curves of FIG. 16 shifted about +2 days along the x-axis.

For comparison in FIGS. 17 and 18 the curves for viable cell density and viability are shifted for about +2 days to show the comparability of the cultivations. This provides evidence for the fact that the use of the separation apparatus as reported herein has no influence on the growth characteristics of the cells.

Figure 19:
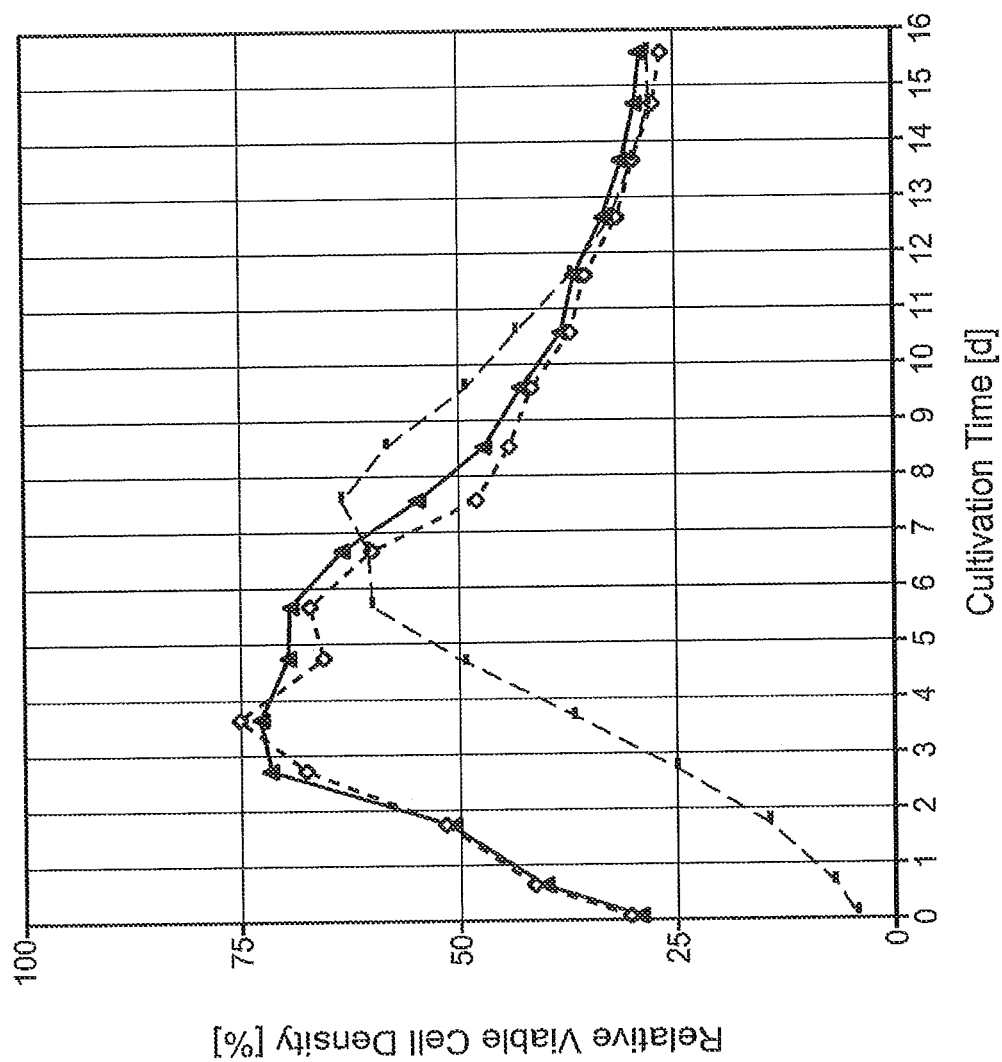
FIG. 19 shows the course of the viable cell density of cultivations starting at an inoculation cell density of 666%: Cell growth of two 2 L cultivations (♦/▲) compared to a 10,000 L process (black dashed line; inoculation cell density of 100%).
Figure 20:
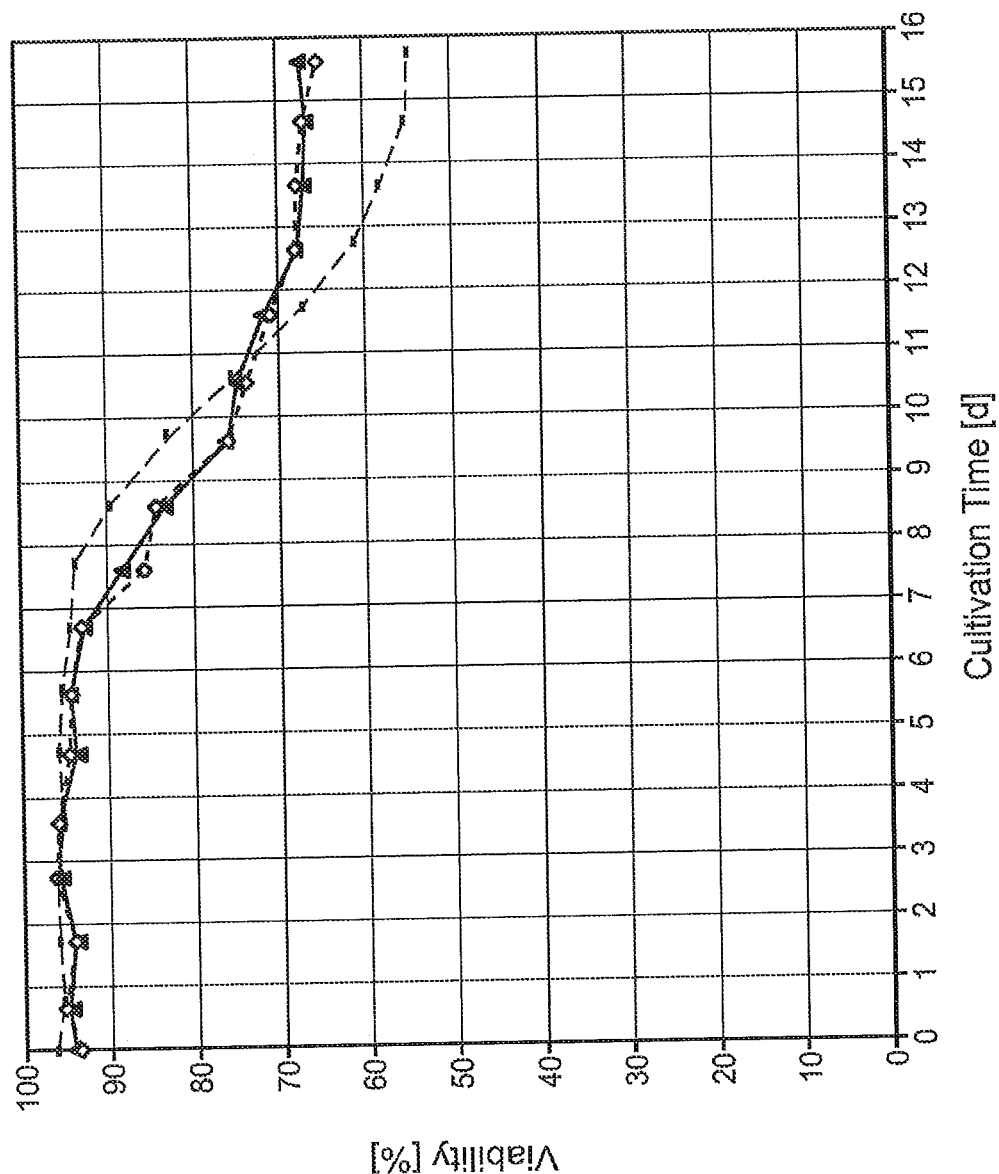
FIG. 20 shows the course of the viability of cultivations starting at an inoculation cell density of 666%: Viability two of 2 L cultivations (♦/▲) compared to a 10,000 L process (black dashed line; inoculation cell density of 100%).
Figure 21:
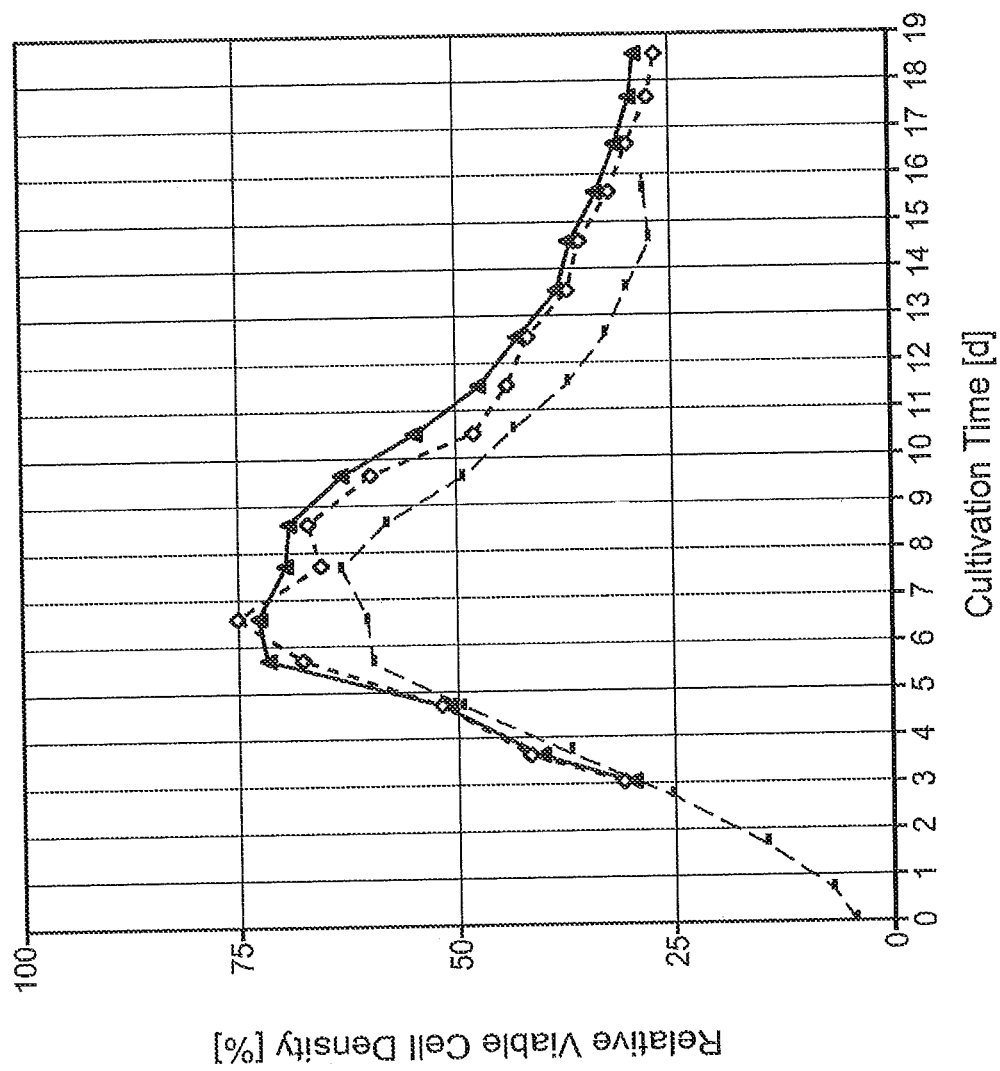
FIG. 21 shows curves of FIG. 19 shifted for about +3 days along the x-axis.
Figure 22:
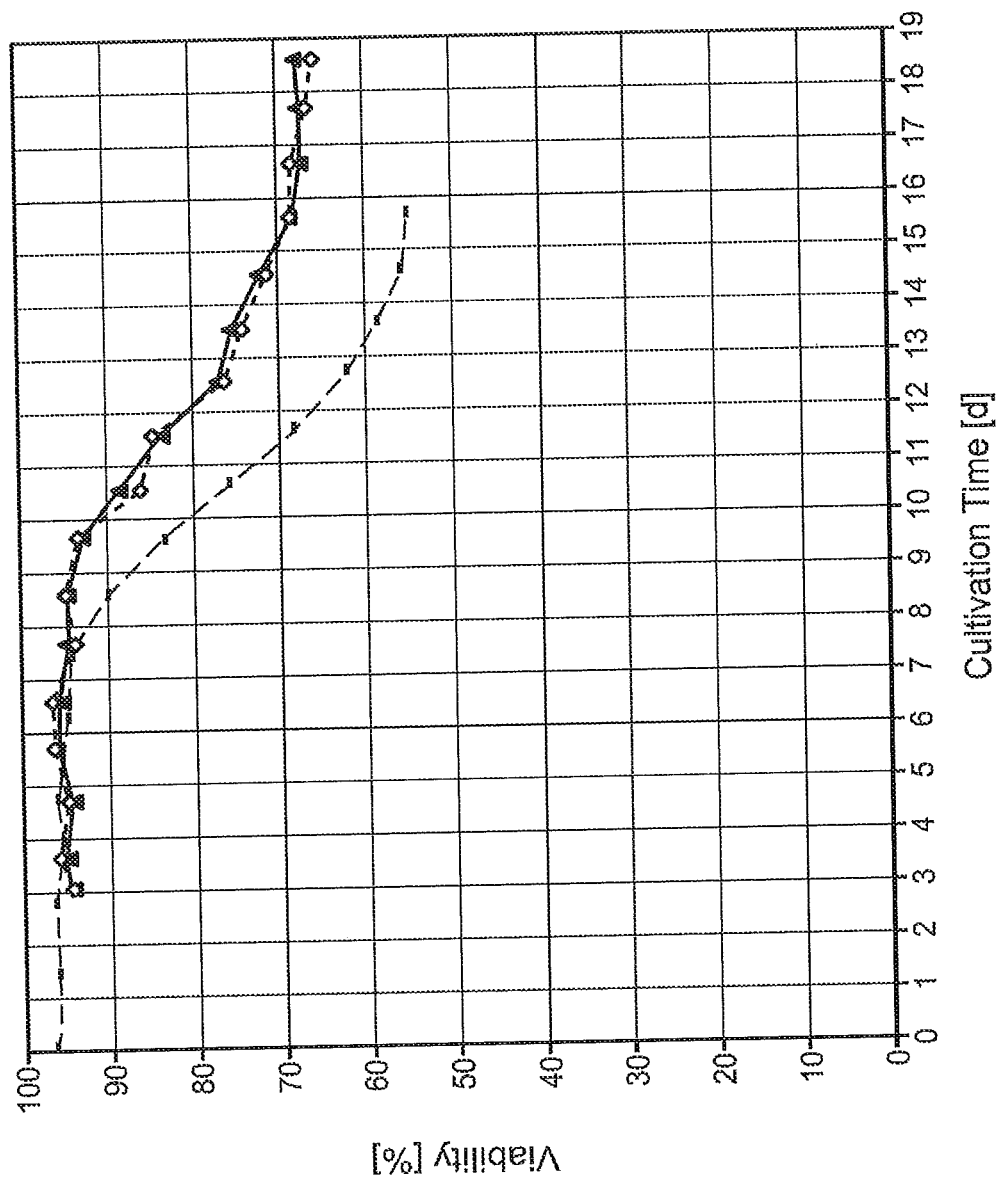
FIG. 22 shows curves of FIG. 20 shifted for about +3 days along the x-axis
Figure 23:
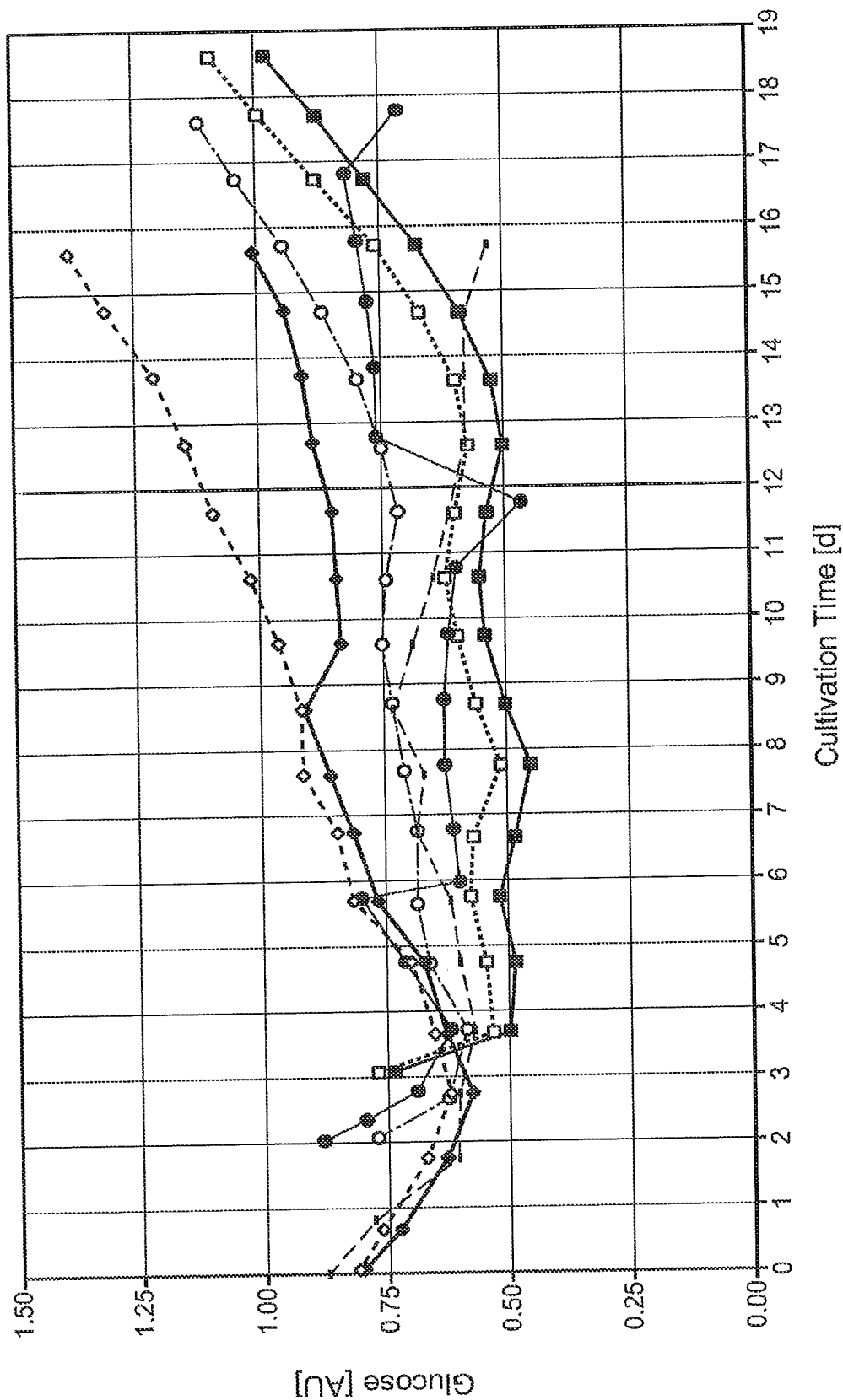
FIG. 23 shows the course of the glucose concentration determined for different inoculation cell densities (ICD). 10,000 L process (black dashed line; inoculation cell density of 100%); 2 L fermentations (♦/ICD 100%); 2 L and 400 L fermentations (○/●/ICD 333%) and 2 L fermentation (♦/ICD 666%).
Figure 24:
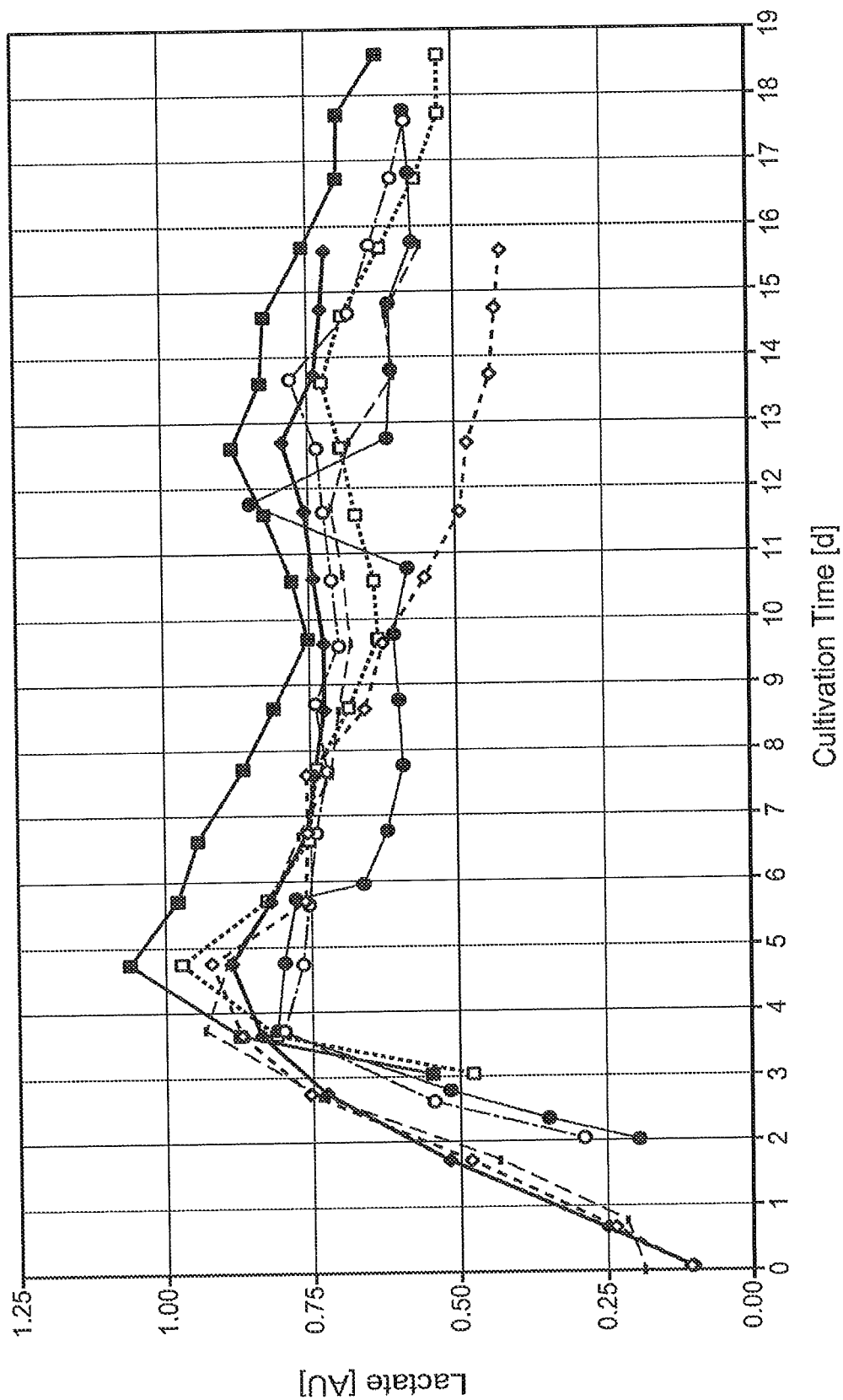
FIG. 24 shows the course of the lactate concentration determined for different inoculation cell densities (ICD). 10,000 L process (black dashed line; inoculation cell density of 100%); 2 L fermentations (♦/ICD 100%); 2 L and 400 L fermentations (○/●/ICD 333%) and 2 L fermentation (■/ICD 666%).
Figure 25:
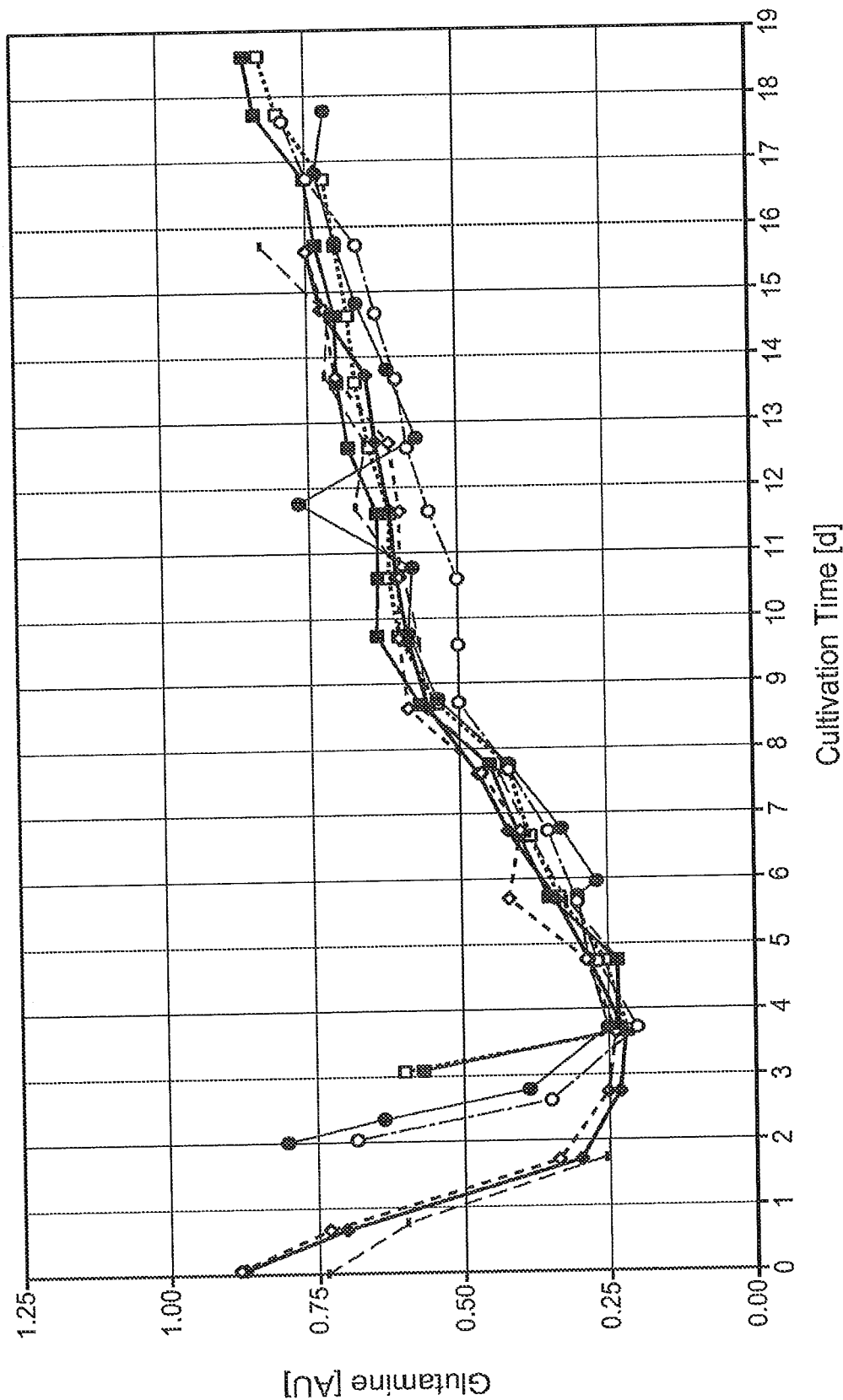
FIG. 25 shows the course of the glutamine concentration determined for different inoculation cell densities (ICD). 10,000 L process (black dashed line; inoculation cell density of 100%); 2 L fermentations (■/ICD 100%); 2 L and 400 L fermentations (○/●/ICD 333%) and 2 L fermentation (■/ICD 666%).
Figure 26:
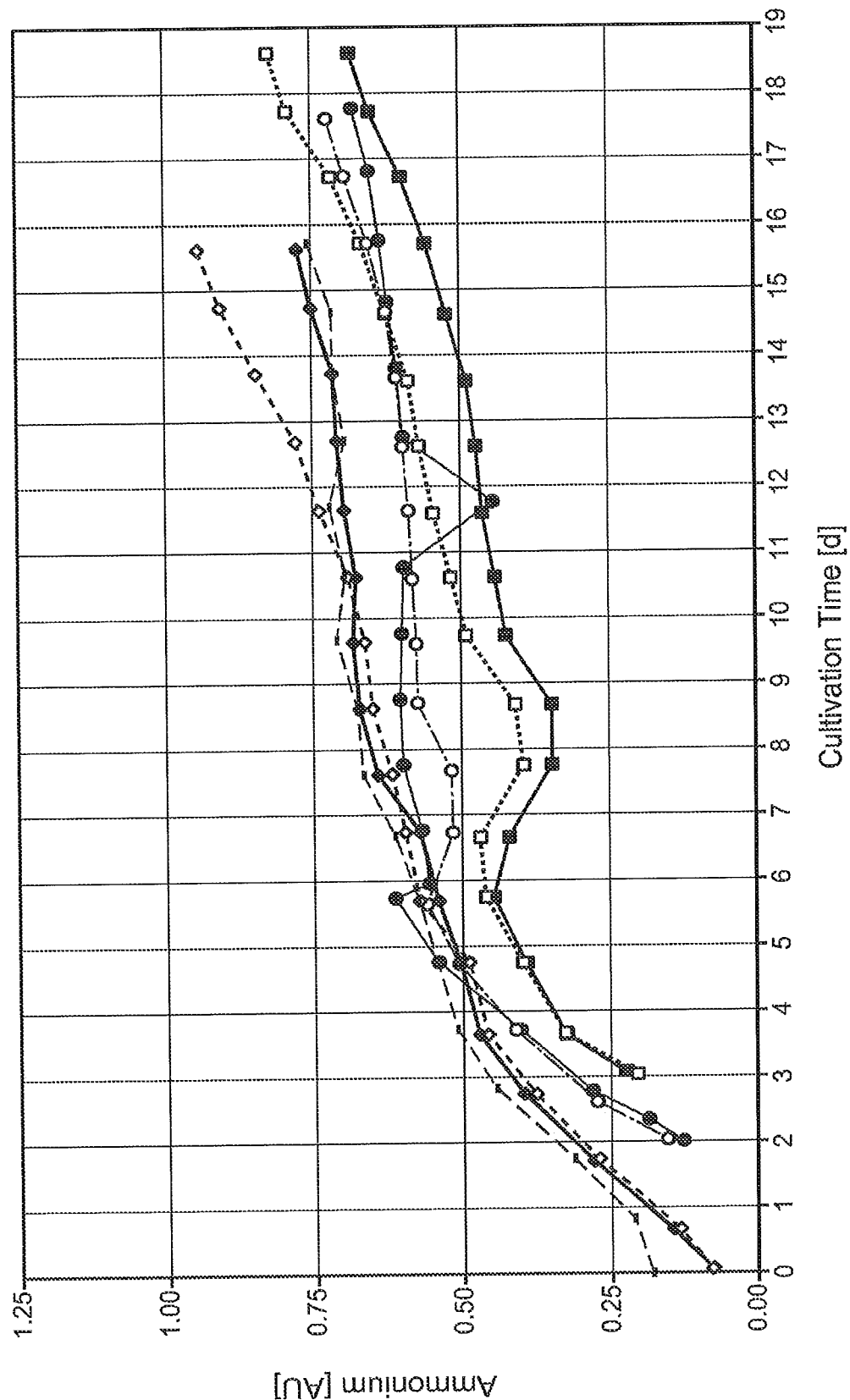
FIG. 26 shows the course of the ammonium concentration determined for different inoculation cell densities (ICD).

Analogous results have been obtained with an inoculation cell density of 666% as shown in FIGS. 19/20 and FIGS. 21/22. Therein the cell growth and viabilities of two 2 L cultivations with an inoculation cell density of 666% is shown. As can be seen is the maximum cell density was already reached after 4 days of cultivation, which reduced the process time for about 3 days (shown in FIG. 21/22 in which the curves of FIG. 19/20 are shifted for about +3 days). Thus, at an inoculation cell density of 666% the separation apparatus has no influence on cell growth and viability in a subsequent cultivation.

No lag phase of the cell growth with an inoculation cell density of 666% was observed. No cell growth limitation or inhibitions could be recognized by using the settler to provide a concentrated cell suspension to inoculate at an increased cell density of 666%. No negative effects of the apparatus and his equipment were observed 1.4.2 Antibody Production The product concentration over the cultivation time of the 2 L cultivations with an inoculation cell density of 100% is shown in FIG. 28. A comparison of the higher inoculated curves clearly depict, that the overall process time can be reduced by 4 to 5 days by using the separation apparatus as reported herein with higher inoculation cell densities.

Thus, as outlined in the sections above by using a separation apparatus as reported herein in the N−1 seed train fermentation the main cultivation can be inoculated at higher cell densities. Furthermore, although the cells grow to higher cell densities in the N−1 seed train fermentation no lag phase can be observed after the inoculation of the main cultivation. The cells immediately start to grow in an exponential way. Therewith the corresponding values with regard to cell density and product concentration when compared to a reference production fermentation without using the separation apparatus in the N−1 seed train fermentation were reached at an earlier point in time during the cultivation. The cell culture performance and product titers show no significant differences and allow a total shortening of the operation time by at least 2 or at least 4 days, respectively, depending on the inoculation cell densities. Using this process as an example the production time can be shortened by 25%.

2. Results

The invention relates to a novel sedimentation apparatus that is, inter alia, suitable for large scale (for example, 2,000 L/day to 3,000 L/day-level) usage in cell cultivation and cell separation.

Concerning higher cell density in the seed train of the N−1 step a good comparability of the cell growth between main cultivations using the separation apparatus in the seed train fermentation and those not using it could be illustrated beside the fact that the curves for those main cultivations using the separation apparatus in the seed train can be shortened by 2 to 4 days compared to the reference process (established production process).

The apparatus did not affect the cell culture leading to high retention rates.

The gist of the invention is the provision of comparable cell growth (no lag phase) and a stable product quantity in the following production culture (N step) by using a higher inoculation cell density for higher time-space yield with the apparatus of this invention.

All different inoculation cell densities showed no lag phase or inhibitions after inoculation with a cell suspension obtained by using the apparatus of the invention.

Summarizing the above, by using a separation apparatus as reported herein it is possible to reduce the required time of the main fermentation by at least about 2 to 4 days without negative impact on product concentration. Thus, by the overall reduction in time required for a single production campaign, i.e. seed train fermentation and main fermentation, more campaigns can be performed in the same time, e.g. one year, or an expansion of the production facilities, i.e. bioreactor volumes, can be avoided.

What is claimed is:

1. A system, comprising:
a bioreactor for growth of cells in a cell suspension;
a separating apparatus located downstream of the bioreactor for separation of suspended cells from the cell suspension; wherein the separating apparatus comprises:
a sedimentation settler having a plurality of channels; and
a collection vessel disposed underneath and being in fluid communication with the sedimentation settler, the collection vessel forming a receiving chamber having an outlet at or adjacent to a chamber bottom and having an inflow inlet opening above the outlet, wherein:
an inner wall of the collection vessel extending from the outlet to the inflow inlet opening is curved such that a horizontal cross-sectional area decreases towards the chamber bottom,
the inflow inlet opening is located at the same vertical height level of the separating apparatus as a lower edge of the sedimentation settler or below the lower edge of the sedimentation settler,
the collection vessel is arranged such that a flow direction of a fluid inflow from the inflow inlet opening into the receiving chamber is substantially in line with the direction of the channels of the sedimentation settler after passing the inflow inlet opening, and
  (1) the collection vessel comprises a baffle plate located at or in proximity to the inflow inlet opening and extending down into the collection vessel to a distance less than half of a depth of the collection vessel, the baffle plate for downwardly deflecting the fluid inflow after passing the inflow inlet opening, wherein (i) an arrangement and shape of the baffle plate and a curvature of the inner wall of the collection vessel are adapted to each other such that an initially downwardly deflected fluid inflow is further guided up towards the sedimentation settler, (ii) the baffle plate extends from a lower portion of the sedimentation settler at the lower edge of the sedimentation settler closest to the inflow inlet opening, or (iii) the baffle plate is connected to an inner wall of the collection vessel above the inflow inlet opening; or
  (2) the system further comprises a rotor located upstream of the inflow inlet opening, the rotor comprising one or more vanes to set the fluid inflow in rotation.

2. The system of claim 1, further comprising an electromagnetic vibrator attached to the separating apparatus.

3. The system of claim 1, further comprising a heat exchanger located between the bioreactor and the separating apparatus.

4. The system of claim 1, wherein the collection vessel comprises the baffle plate, the baffle plate being located at or in proximity to the inflow inlet opening and extending down into the collection vessel to the distance less than half of the depth of the collection vessel, the baffle plate downwardly deflecting the fluid inflow after passing the inflow inlet opening.

5. The system of claim 4, wherein the baffle plate is arranged at an incline relative to a first imaginary vertical plane ($V_1$) that is perpendicular to a second imaginary vertical plane ($V_2$) comprising a fluid inflow direction axis through the inflow inlet opening.

6. The system of claim 4, wherein the arrangement and shape of the baffle plate and the curvature of the inner wall of the collection vessel are adapted to each other such that the initially downwardly deflected fluid inflow is further guided up towards the sedimentation settler.

7. The system of claim 5, wherein the baffle plate is inclined such that it intersects said first imaginary vertical plane ($V_1$) along a horizontal line ($H_1$).

8. The system of claim 4, wherein an inclination ($\alpha$) of the baffle plate is the same as an inclination ($\alpha'$) of the channels of the sedimentation settler.

9. The system of claim 4, wherein the baffle plate extends from the lower portion of the sedimentation settler at the lower edge of the sedimentation settler closest to the inflow inlet opening.

10. The system of claim 4, wherein the baffle plate is connected to the inner wall of the collection vessel above the inflow inlet opening.

11. The system of claim 1, comprising the rotor.

12. The system of claim 1, wherein the sedimentation settler comprises a plurality of plates defining the channels in between.

13. The system of claim 1, wherein the volume of the collection vessel is within a range of 1 to 20 m$^3$.

14. A separating apparatus for separation of suspended cells from the cell suspension, wherein the separating apparatus comprises:
  a sedimentation settler having a plurality of channels; and
  a collection vessel disposed underneath and being in fluid communication with the sedimentation settler, the collection vessel forming a receiving chamber having an outlet at or adjacent to a chamber bottom and having an inflow inlet opening above the outlet,
  wherein:
    an inner wall of the collection vessel extending from the outlet to the inflow inlet opening is curved such that a horizontal cross-sectional area decreases towards the chamber bottom,
    the inflow inlet opening is located at the same vertical height level of the separating apparatus as the lower edge of the sedimentation settler or below the lower edge of the sedimentation settler,
    the collection vessel is arranged such that a flow direction of a fluid inflow from the inflow inlet opening into the receiving chamber is substantially in line with the direction of the channels of the sedimentation settler after passing the inflow inlet opening, and
    (1) the collection vessel comprises a baffle plate located at or in proximity to the inflow inlet opening and extending down into the collection vessel to a distance less than half of a depth of the collection vessel, the baffle plate for downwardly deflecting the fluid inflow after passing the inflow inlet opening, wherein (i) an arrangement and shape of the baffle plate and a curvature of the inner wall of the collection vessel are adapted to each other such that an initially downwardly deflected fluid inflow is further guided up towards the sedimentation settler, (ii) the baffle plate extends from a lower portion of the sedimentation settler at the lower edge of the sedimentation settler closest to the inflow inlet opening, or (iii) the baffle plate is connected to an inner wall of the collection vessel above the inflow inlet opening; or
    (2) the system further comprises a rotor located upstream of the inflow inlet opening, the rotor comprising one or more vanes to set the fluid inflow in rotation.

15. The separating apparatus of claim 14, wherein the volume of the collection vessel is within a range of 1 to 20 m$^3$.

16. A method for cultivation of suspended cells in a cell suspension in the system of claim 1, the method comprising:
  inoculating the suspended cells in medium contained in the bioreactor to achieve an inoculation cell density of $5\times10^5$ cells/ml to $50\times10^5$ cells/ml; and
  passing the cell suspension through the separating apparatus to separate cells for return to the bioreactor.

17. The method of claim 16, wherein a volume of cell suspension volume passed through the separating apparatus is from 500 liters/day to 3,000 liters/day.

18. A method for cultivation of suspended cells in a cell suspension, the method comprising:
  (a) providing a system comprising (i) a bioreactor for growth of cells in a cell suspension; and (ii) a separating apparatus located downstream of the bioreactor for separation of suspended cells from the cell suspension; wherein the separating apparatus comprises:

a sedimentation settler having a plurality of channels; and
a collection vessel disposed underneath and being in fluid communication with the sedimentation settler, the collection vessel forming a receiving chamber having an outlet at or adjacent to a chamber bottom and having an inflow inlet opening above the outlet,
wherein:
  an inner wall of the collection vessel extending from the outlet to the inflow inlet opening is curved such that a horizontal cross-sectional area decreases towards the chamber bottom,
  the inflow inlet opening is located at the same vertical height level of the separating apparatus as the lower edge of the sedimentation settler or below the lower edge of the sedimentation settler,
    the collection vessel is arranged such that a flow direction of a fluid inflow from the inflow inlet opening into the receiving chamber is substantially in line with the direction of the channels of the sedimentation settler after passing the inflow inlet opening, and
    (1) the collection vessel comprises a baffle plate located at or in proximity to the inflow inlet opening and extending down into the collection vessel to a distance less than half of a depth of the collection vessel, the baffle plate for downwardly deflecting the fluid inflow after passing the inflow inlet opening, wherein (i) an arrangement and shape of the baffle plate and a curvature of the inner wall of the collection vessel are adapted to each other such that an initially downwardly deflected fluid inflow is further guided up towards the sedimentation settler, (ii) the baffle plate extends from a lower portion of the sedimentation settler at the lower edge of the sedimentation settler closest to the inflow inlet opening, or (iii) wherein the baffle plate is connected to an inner wall of the collection vessel above the inflow inlet opening; or
    (2) the system further comprises a rotor located upstream of the inflow inlet opening, the rotor comprising one or more vanes to set the fluid inflow in rotation;
(b) inoculating the suspended cells in medium contained in the bioreactor to achieve an inoculation cell density of $5 \times 10^5$ cells/ml to $50 \times 10^5$ cells/ml; and
(c) passing the cell suspension through the separating apparatus to separate cells from a clear phase, wherein separated cells are returned to the bioreactor.

19. The method of claim 18, wherein a volume of cell suspension volume passed through the separating apparatus is from 500 liters/day to 3,000 liters/day.

* * * * *